(12) United States Patent
Mobashery et al.

(10) Patent No.: US 9,045,442 B2
(45) Date of Patent: Jun. 2, 2015

(54) ANTIBACTERIAL COMPOUNDS AND METHODS OF USING SAME

(75) Inventors: Shahriar Mobashery, Notre Dame, IN (US); Peter I. O'Daniel, Notre Dame, IN (US); Mayland Chang, Notre Dame, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 1149 days.

(21) Appl. No.: 12/680,541

(22) PCT Filed: Dec. 21, 2007

(86) PCT No.: PCT/US2007/088602
§ 371 (c)(1), (2), (4) Date: Mar. 26, 2010

(87) PCT Pub. No.: WO2009/082398
PCT Pub. Date: Jul. 2, 2009

(65) Prior Publication Data
US 2010/0261673 A1      Oct. 14, 2010

Related U.S. Application Data

(63) Continuation-in-part of application No. PCT/US2007/079672, filed on Sep. 27, 2007.

(51) Int. Cl.
| | | |
|---|---|---|
| C07D 271/06 | (2006.01) | |
| C07D 403/12 | (2006.01) | |
| C07D 413/12 | (2006.01) | |
| C07F 9/653 | (2006.01) | |

(52) U.S. Cl.
CPC ............ *C07D 271/06* (2013.01); *C07D 413/12* (2013.01); *C07F 9/65318* (2013.01)

(58) Field of Classification Search
None
See application file for complete search history.

(56) References Cited

U.S. PATENT DOCUMENTS

| | | | | |
|---|---|---|---|---|
| 6,277,872 B1 * | 8/2001 | Brenner et al. | ............... | 514/364 |
| 6,737,248 B2 | 5/2004 | Kunsch et al. | | |

FOREIGN PATENT DOCUMENTS

| | | |
|---|---|---|
| EP | 1501515 B1 | 11/2005 |
| WO | 03007955 A2 | 1/2003 |
| WO | 03040112 A1 | 5/2003 |
| WO | 03087044 A2 | 10/2003 |
| WO | 03087045 A1 | 10/2003 |
| WO | 03087046 A1 | 10/2003 |
| WO | 2004048319 A1 | 6/2004 |
| WO | WO 2005/115382 A1 * | 12/2005 |
| WO | 2007085451 A2 | 8/2007 |
| WO | 2008097428 A2 | 8/2008 |
| WO | 2009041972 A1 | 4/2009 |
| WO | 2009082398 A1 | 7/2009 |

OTHER PUBLICATIONS

Patil et al. Journal of the Indian Chemical Society (1979), 56(12), pp. 1243-1245.*
Nururkar et al. Bulletin of Haffkine Institute (1980), 8(1), pp. 27-32 (STN Abstract attached).*
Pachhamia et al. Journal of the Indian Chemical Society (1989), 66(4), pp. 250-251.*
Pavagadhi et al. Oriental Journal of Chemistry (2001), 17(2), pp. 311-314 (STN Abstract attached).*
Zhou et al. Synthetic Communications, 2002, vol. 32, No. 6, pp. 887-891.*
Corsaro et al. (Tetrahedron, 1996, vol. 52, No. 23, pp. 7885-7892.*

* cited by examiner

*Primary Examiner* — James D Anderson
(74) *Attorney, Agent, or Firm* — Haukaas Fish PLLC; Michael H. Haukaas

(57) ABSTRACT

Embodiments of the present invention provide novel antibacterials that target penicillin-binding proteins or other important cellular targets. Methods for inhibiting growth (reproduction, etc.) of bacteria using compounds described herein are also provided. Various embodiments exhibit activity against gram positive bacteria, such as certain strains of *Entercoccus* and *Staphylococcus aureus*.

10 Claims, 3 Drawing Sheets

Reagents: a) CuI, Cs$_2$CO$_3$, N,N-dimethylglycine HCl, 1,4-dioxane, 90°C; b) Hydroxylamine, ethanol, reflux, 3h;

Reagents: a) NEt(Ip)₂, CH₂Cl₂, 0°C -> rt; b) i EDC, CH₂Cl₂, ii (Bu)₄NF, rt; c) THF, (Bu)₄NF, rt, 24h; d) 10% Pd/C, MeOH, THF, H₂, 24h.

ANTIBACTERIAL COMPOUNDS AND METHODS OF USING SAME

GOVERNMENT INTEREST

This invention was made with Government support under Contract No. GM061629 awarded by the National Institutes of Health. The Government has certain rights in the invention.

CROSS REFERENCE TO RELATED APPLICATIONS

The present application is a 35 U.S.C. 371 national stage entry of PCT Application No. PCT/US07/088602, filed Dec. 21, 2007, entitled "ANTIBACTERIAL COMPOUNDS AND METHODS OF USING SAME," and claims priority to co-pending PCT Application No. PCT/US07/079672, filed Sep. 27, 2007, entitled "ANTIBACTERIAL COMPOUNDS AND METHODS OF USING SAME," the entire contents of which are hereby incorporated by reference in their entirety.

TECHNICAL FIELD

Embodiments of the present invention relate to the field of chemistry and biochemistry, and, more specifically, to antibacterial compounds and methods of using antibacterial compounds.

BACKGROUND

Penicillin-binding proteins (PBPs) are a group of proteins characterized by their affinity for and binding of penicillin. PBPs do not just bind penicillin, but rather bind all beta-lactam antibiotics, which are a family of antibiotics sharing a four membered lactam ring.

There are a large number of PBPs, usually several in each organism, and they are found mostly as membrane-bound proteins, but a few are known to be non-membrane associated. Different PBPs occur in different numbers per cell and have varied affinities for different kinds of β-lactam antibiotics. PBPs are involved in the final stages of the synthesis of peptidoglycan, which is the major component of bacterial cell walls. Bacterial cell wall synthesis is essential to growth, cell division (thus reproduction), and maintenance of the cellular structure in bacteria. Inhibition of PBPs leads to irregularities in bacterial cell wall structure such as elongation, lesions, loss of selective permeability, and eventual cell death and lysis. Bacterial cell wall synthesis, and in particular PBPs, provides a good target for drugs of selective toxicity because the metabolic pathways and enzymes are unique to bacteria.

BRIEF DESCRIPTION OF THE DRAWINGS

Embodiments of the present invention will be readily understood by the following detailed description in conjunction with the accompanying drawings. Embodiments of the invention are illustrated by way of example and not by way of limitation in the figures of the accompanying drawings.

DETAILED DESCRIPTION OF EMBODIMENTS OF THE INVENTION

Figure 1:
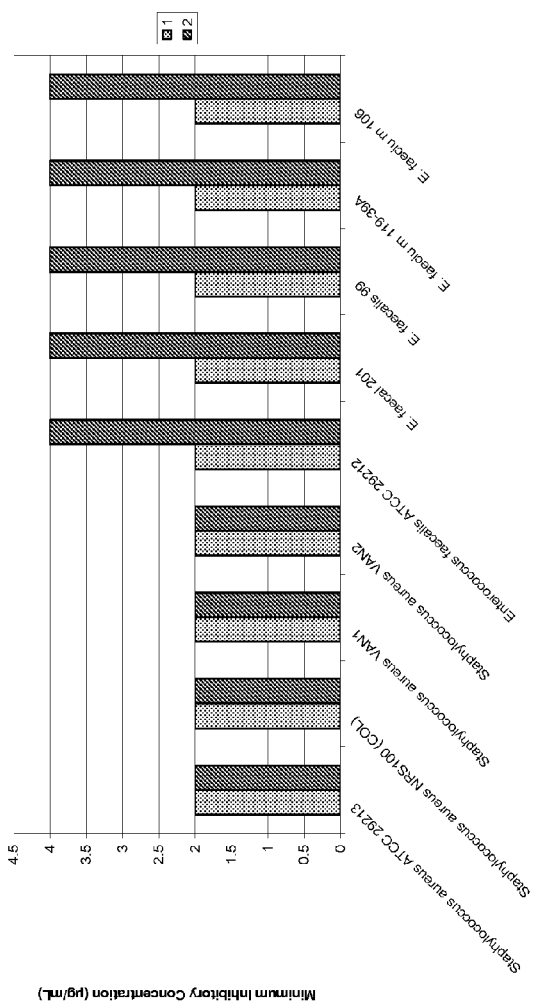
FIG. 1 illustrates the minimum inhibitory concentration (μg/mL) for two compounds tested against various strains of *Staphylococcus aureus* and *Entercoccus* in accordance with various embodiments of the present invention.

In the following detailed description, reference is made to the accompanying drawings that form a part hereof, and in which are shown by way of illustration embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

The description may use perspective-based descriptions such as up/down, back/front, and top/bottom. Such descriptions are merely used to facilitate the discussion and are not intended to restrict the application of embodiments of the present invention.

For the purposes of the description, a phrase in the form "A/B" or in the form "A and/or B" means "(A), (B), or (A and B)". For the purposes of the description, a phrase in the form "at least one of A, B, and C" means "(A), (B), (C), (A and B), (A and C), (B and C), or (A, B and C)". For the purposes of the description, a phrase in the form "(A)B" means "(B) or (AB)" that is, A is an optional element.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

As used herein, the term "halogen" refers to F, Cl, Br and I.

As used herein, the term "hydroxyl" refers to a moiety containing one or more OH.

As used herein, the term "cyano" refers to a moiety containing one or more —C≡N.

As used herein, the term "alkyl" refers to both straight- and branched-chain moieties.

As used herein, the term "alkenyl" refers to both straight- and branched-chain moieties containing one or more —C═C—.

As used herein, the term "alkynyl" refers to both straight- and branched-chain moieties containing one or more —C≡C—.

As used herein, the term "alkoxy" refers to —O-alkyl groups.

As used herein, the term "aryloxy" refers to —O-aryl groups.

As used herein, the term "cycloalkyl" refers to a cyclic alkyl moiety. Unless otherwise stated cycloalkyl moieties include between 3 and 8 carbon atoms.

As used herein, the term "cycloalkenyl" refers to a cyclic alkenyl moiety. Unless otherwise stated cycloalkenyl moieties include between 3 and 8 carbon atoms and one or more —C═C— within the cyclic ring.

As used herein, the term "amino" refers to $NH_2$, NHR, or $NR_2$. Unless otherwise stated R can be alkyl, alkenyl, alkynyl, cycloalkyl, cycloalkenyl, het or aryl.

As used herein, the term "nitro" refers to $NO_2$.

As used herein, the term "phosphate" refers to but is not limited to —O—P—$(OH)_3$, —O—P—$(OH)_2$ONa, —O—P—$(ONa)_2$OH, —O—P—$(ONa)_3$, —O—P—$(OH)_2$OK, —O—P—$(OK)_2$OH, —O—P—$(OK)_3$ or a free acid or a pharmaceutically acceptable salt.

As used herein, the term "aryl" refers to phenyl and naphthyl.

As used herein, the term "sulfhydryl" refers to —SH.

As used herein, the term "het" refers to a mono- or bi-cyclic ring system containing one or more heteroatom selected from O, S, and N. Each mono-cyclic ring may be aromatic, saturated or partially unsaturated. A bi-cyclic ring system may include a mono-cyclic ring containing one or more heteroatom fused with a cycloalkyl or aryl group. A bi-cyclic ring system may also include a mono-cyclic ring containing one or more heteroatom fused with another het, mono-cyclic ring system.

Examples of "het" include but are not limited to pyridine, thiophene, furan, pyrazoline, pyrrole, pyrazoline, pyrimidine, 2-pyridyl, 3-pyridyl, 4-pyridyl, 2-pyrimidinyl, 4-pyrimidinyl, 5-pyrimidinyl, 3-pyrazinyl, 3-pyridazinyl, 4-pyridazinyl, 4-oxo-2-imidazolyl, 1,2,4-oxadiazole, 1,3,4-oxadiazole, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,5-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, benzoxazoyl, diazinyl, triazinyl, quinolinyl, quinoxalinyl, naphthyridinyl, azetidinyl, pyrrolidinyl, hydantoinyl, oxathiolanyl, dioxolanyl, imidazolidinyl, and azabicyclo [2.2.1] heptyl.

As used herein, the term "heteroaryl" refers to a mono- or bicyclic het in which one or more cyclic ring is aromatic.

As used herein, the term "substituted heteroaryl" refers to a heteroaryl moiety substituted with one or more functional groups selected from halogen, alkyl, hydroxyl, amino, alkoxy, cyano, and nitro.

As used herein, the term "substituted alkyl" refers to an alkyl moiety including 1-4 substituents selected from halogen, het, cycloalkyl, cycloalkenyl, aryl, amino, cyano, nitro, —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$C(=NOQ_{10})Q_{10}$, —$S(O)_2$—N=$S(O)(Q_{10})_2$, —$S(O)_2$—N=$S(Q_{10})_2$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(S)NQ_{10}Q_{10}$, —$N(Q_{10})C(S)NQ_{10}Q_{10}$, —$C(O)NQ_{10}Q_{10}$, —$C(S)NQ_{10}Q_{10}$, —$C(O)C(Q_{16})_2OC(O)Q_{10}$, —CN, =S, —$NQ_{10}C(O)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, and —$SNQ_{10}Q_{10}$. Each of the het, cycloalkyl, cycloalkenyl, and aryl being optionally substituted with 1-4 substituents independently selected from halogen and $Q_{15}$.

As used herein, the term "substituted aryl" refers to an aryl moiety having 1-3 substituents selected from halogen, het, alkyl, substituted alkyl, alkenyl, alkynyl, alkoxy, cycloalkyl, cycloalkenyl, aryl, cyano, nitro, —$OQ_{10}$, —$SQ_{10}$, —$S(O)_2Q_{10}$, —$S(O)Q_{10}$, —$OS(O)_2Q_{10}$, —$C(=NQ_{10})Q_{10}$, —$C(=NOQ_{10})Q_{10}$, —$S(O)_2$—N=$S(O)(Q_{10})_2$, —$S(O)_2$—N=$S(Q_{10})_2$, —$NQ_{10}Q_{10}$, —$C(O)Q_{10}$, —$C(S)Q_{10}$, —$C(O)OQ_{10}$, —$OC(O)Q_{10}$, —$C(O)NQ_{10}Q_{10}$, —$C(S)NQ_{10}Q_{10}$, —$C(O)C(Q_{16})_2OC(O)Q_{10}$, —$NQ_{10}C(O)Q_{10}$, —$N(Q_{10})C(S)NQ_{10}Q_{10}$, —$N(Q_{10})C(S)Q_{10}$, —$NQ_{10}C(O)NQ_{10}Q_{10}$, —$S(O)_2NQ_{10}Q_{10}$, —$NQ_{10}S(O)_2Q_{10}$, —$NQ_{10}S(O)Q_{10}$, —$NQ_{10}SQ_{10}$, and —$SNQ_{10}Q_{10}$. The het, cycloalkyl, cycloalkenyl, alkenyl, alkynyl, and aryl being optionally substituted with 1-3 substituents selected from halogen and $Q_{15}$.

Each $Q_{10}$ is independently selected from H, alkyl, cycloalkyl, het, cycloalkenyl, and aryl. The het, cycloalkyl, cycloalkenyl, and aryl being optionally substituted with 1-3 substitutents selected from halo and $Q_{13}$.

Each $Q_{11}$ is independently selected from H, halogen, alkyl, aryl, cycloalkyl, and het. The alkyl, aryl, cycloalkyl, and het being optionally substituted with 1-3 substituents independently selected from halogen, nitro, cyano, =S, =O, and $Q_{14}$.

Each $Q_{13}$ is independently selected from $Q_{11}$, —$OQ_{11}$, —$SQ_{11}$, —$S(O)_2Q_{11}$, —$S(O)Q_{11}$, —$OS(O)_2Q_{11}$, —$C(=NQ_{11})Q_{11}$, —$S(O)_2$—N=$S(O)(Q_{11})_2$, —$S(O)_2$—N=$S(Q_{11})_2$, —$SC(O)Q_{11}$, —$NQ_{11}Q_{11}$, —$C(O)Q_{11}$, —$C(S)Q_{11}$, —$C(O)OQ_{11}$, —$OC(O)Q_{11}$, —$C(O)NQ_{11}Q_{11}$, —(S)$NQ_{11}Q_{11}$, —$C(O)C(Q_{16})_2OC(O)Q_{10}$, —CN, =O, =S, —$NQ_{11}C(O)Q_{11}$, —$NQ_{11}C(S)Q_{11}$, —$NQ_{11}C(O)NQ_{11}Q_{11}$, —$NQ_{11}C(S)NQ_{11}Q_{11}$, —$S(Q)_2NQ_{11}Q_{11}$, —$NQ_{11}S(O)_2Q_{11}$, —$NQ_{11}S(O)Q_{11}$, —$NQ_{11}SQ_{11}$, —$NO_2$, and —$SNQ_{11}Q_{11}$.

Each $Q_{14}$ is independently selected from H, alkyl, cycloalkyl, phenyl, or naphthyl, each optionally substituted with 1-4 substituents independently selected from F, Cl, Br, I, —$OQ_{16}$, —$SQ_{16}$, —$S(O)_2Q_{16}$, —$S(O)Q_{16}$, —$OS(O)_2Q_{16}$, —$NQ_{16}Q_{16}$, —$C(O)Q_{16}$, —$C(S)Q_{16}$, —$C(O)OQ_{16}$, —$NO_2$, —$C(O)NQ_{16}Q_{16}$, —$C(S)NQ_{16}Q_{16}$, —CN, —$NQ_{16}C(O)Q_{16}$, —$NQ_{16}C(S)Q_{16}$, —$NQ_{16}C(O)NQ_{16}Q_{16}$, —$NQ_{16}C(S)NQ_{16}Q_{16}$, —$S(O)_2NQ_{16}Q_{16}$, and —$NQ_{16}S(O)_2Q_{16}$. The alkyl, cycloalkyl, and cycloalkenyl being further optionally substituted with =O or =S.

Each $Q_{15}$ is independently selected from H, alkyl, cycloalkyl, heteroaryl, phenyl, or naphthyl, each optionally substituted with 1-4 substituents independently selected from F, Cl, Br, I, —$OQ_{16}$, —$SQ_{16}$, —$S(O)_2Q_{16}$, —$S(O)Q_{16}$, —$OS(O)_2Q_{16}$, —$C(=NQ_{16})Q_{16}$, —$S(O)_2$—N=$S(O)(Q_{16})_2$, —$S(O)_2$—N=$S(Q_{16})_2$, —$SC(O)Q_{16}$, —$NQ_{16}Q_{16}$, —$C(O)Q_{16}$, —$C(S)Q_{16}$, —$C(O)OQ_{16}$, —$OC(O)Q_{16}$, —$C(S)NQ_{16}Q_{16}$, —$C(O)C(Q_{16})_2OC(O)Q_{16}$, —CN, —$NQ_{16}C(O)Q_{16}$, —$NQ_{16}C(S)Q_{16}$, —$NQ_{16}C(O)NQ_{16}Q_{16}$, —$NQ_{16}C(S)NQ_{16}Q_{16}$, —$S(O)_2NQ_{16}Q_{16}$, —$NQ_{16}S(O)_2Q_{16}$, —$NQ_{16}S(O)Q_{16}$, —$NQ_{16}SQ_{16}$, —$NO_2$, and —$SNQ_{16}Q_{16}$. The alkyl, cycloalkyl, and cycloalkenyl being further optionally substituted with =O or =S.

Each $Q_{16}$ is independently selected from H, alkyl, and cycloalkyl. The alkyl and cycloalkyl optionally including 1-3 halogens.

Embodiments of the present invention provide novel antibacterials. In an embodiment, antibacterials are provided that target penicillin-binding proteins (PBPs). In other embodiments, the antibacterials provided herein may inhibit other biochemical processes of bacteria.

In embodiments, the antibacterials of this invention may have useful activity against a variety of organisms. The in vitro activity of compounds of this invention may be assessed by standard testing procedures such as the determination of minimum inhibitory concentration (MIC) by agar dilution.

In embodiments, the antibacterials described herein may be useful for sterilization, sanitation, antisepsis, and disinfection. In an embodiment, the antibacterials may be applied to a location in need of sterilization, sanitation, antisepsis, or disinfection, by methods known to those skilled in the art. For instance, the antibacterials may be incorporated into a cleaning solution that is applied, such as by spraying or pouring, to an item in need of sterilization, sanitation, antisepsis, or disinfection. The antibacterials may be used alone or in combination. In an embodiment, the antibacterials may be applied in varying concentrations depending upon the bacterial susceptibility to the antibacterials being applied and the desired level of sterilization, sanitation, antisepsis, or disinfection.

In an embodiment, the antibacterial compounds may be incorporated into a pharmaceutical composition. In embodiments, certain antibacterials described herein may be useful for treating microbial infections in mammals, such as by administering an effective amount of the antibacterial compound to the mammal.

Embodiments of the present invention encompass any racemic, optically-active, polymorphic, tautomeric, or stereoisomeric form, or mixture thereof, of a compound of the invention, which possesses the useful properties described herein.

In cases where compounds are sufficiently basic or acidic to form stable nontoxic acid or base salts, use of the compounds as pharmaceutically acceptable salts may be appropriate. Examples of pharmaceutically acceptable salts within the scope of embodiments of the present invention include organic acid addition salts formed with acids which form a physiological acceptable anion and inorganic salts.

Pharmaceutical compositions in accordance with embodiments of the invention may be prepared by combining the disclosed compounds with a solid or liquid pharmaceutically acceptable carrier and, optionally, with pharmaceutically acceptable adjuvants and excipients employing standard and conventional techniques. Solid form compositions include powders, tablets, dispersible granules, capsules, cachets and suppositories. A solid carrier may be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water and water-propylene glycol systems, optionally containing suitable conventional coloring agents, flavoring agents, stabilizers and thickening agents.

In an embodiment, a pharmaceutical composition may be provided employing conventional techniques in unit dosage form containing effective or appropriate amounts of one or more active component. In embodiments, the quantity of active component (compound) in a pharmaceutical composition and unit dosage form thereof may be varied or adjusted widely depending upon the particular application, the potency of the particular compound and the desired concentration. In an embodiment, the quantity of active component may range from 0.5% to 90% by weight of the composition.

In embodiments, in therapeutic use for treating, or combating, bacterial infections in animals, the compounds or pharmaceutical compositions thereof may be administered orally, parenterally and/or topically at a dosage to obtain and maintain a concentration, that is, an amount, or blood-level of active component in the animal undergoing treatment which is antibacterially effective. In an embodiment, such an antibacterially effective amount of dosage of active component may be in the range of about 0.1 to about 100 mg/kg, more preferably about 3.0 to about 50 mg/kg, of body weight/day. It is to be understood that the dosages may vary depending upon the requirements of the patient, the severity of the bacterial infection being treated, and the particular compound being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., 2-4 four times per day.

In an embodiment, an initial antibacterial compound was provided and tested. Such compound is identified below as compound A. Compound A (below) is an inhibitor of gram positive bacteria. Compound A also shows activity against some strains of *Entercoccus*.

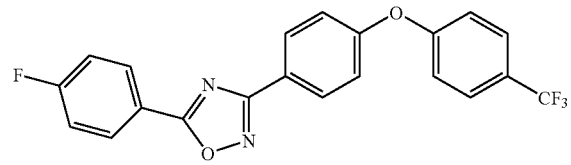

A

Compound A (5-(4-fluorophenyl)-3-(4-(4-(trifluoromethyl)phenoxy)phenyl)-1,2,4-oxadiazole) was synthesized according to following basic protocol. (Z)-4-(4-(Trifluoromethyl)phenoxy)-O-(4-(4-fluorobenzoyl)benzamidoxime (150 mg, 0.358 mmol) was placed in THF (1.5 mL) under an atmosphere of nitrogen. Tetrabutylammonium fluoride (1.0 M, 385 µL) was added dropwise and the solution was stirred at room temperature for 4 hours. The solvent was removed under reduced pressure and the product was purified by column chromatography on silica gel (EtOAc/Hex, 1:3) to give a white solid material (132 mg, 92%). $^1$H NMR (500 MHz, CDCL$_3$) δ(ppm): 7.14 (2H, d, J=9.0 Hz), 7.16 (2H, d, J=9.0 Hz), 7.23-7.27 (2H, m), 7.63 (2H, d, J=8.4 Hz), 8.18 (2H, d, J=8.8 Hz) 8.23 (2H, dd, J=9.0, 5.4 Hz). $^{13}$C NMR (125 MHz, CDCL$_3$) δ(ppm): 116.7 (CH, d, J=15.2 Hz), 119.0 (CH), 119.8 (CH), 120.8 (C, d, J=4.2 Hz), 122.9, 123.2, 125.4, 126.0 (C, q, J=32.5 Hz), 127.6 (CH, q, J=3.8 Hz), 129.7 (CH), 130.8 (CH, d, J=9.0 Hz), 158.8, 159.6, 165.7 (C, d, J=254.1 Hz), 168.5, 175.1. $^{19}$F (282 MHz, CDCL$_3$) δ(ppm): $^-$61.87 (3F, s), $^-$104.90-$^-$105.00 (1F, m). MS (FAB$^+$): 400 (MH$^+$). HRMS for C$_{21}$H$_{12}$F$_4$N$_2$O$_2$ (MH$^+$): calculated: 400.0835; found 400.0811.

Compound A was broken down into smaller structural components and each fraction tested to understand the impact of certain components on the antibacterial properties of the compounds. Based on the understanding of compound A, the compounds (compounds 1 and 2) shown below, were tested further. Compounds 1 and 2 exhibit good activity (as measured by minimum inhibitory concentration testing) against several strains of *Staphylococcus aureus* and *Entercoccus* as shown in FIG. 1. A minimum inhibitory concentration is the lowest concentration of an antimicrobial that will inhibit the visible growth of a microorganism after overnight incubation.

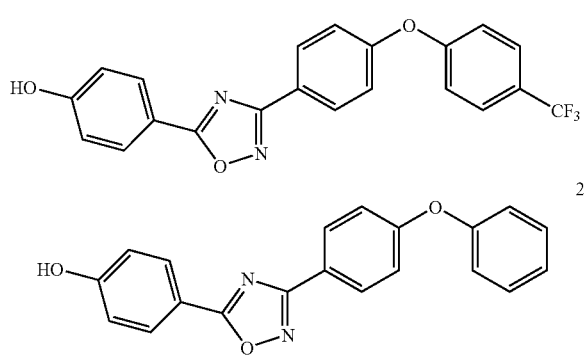

Figure 2:
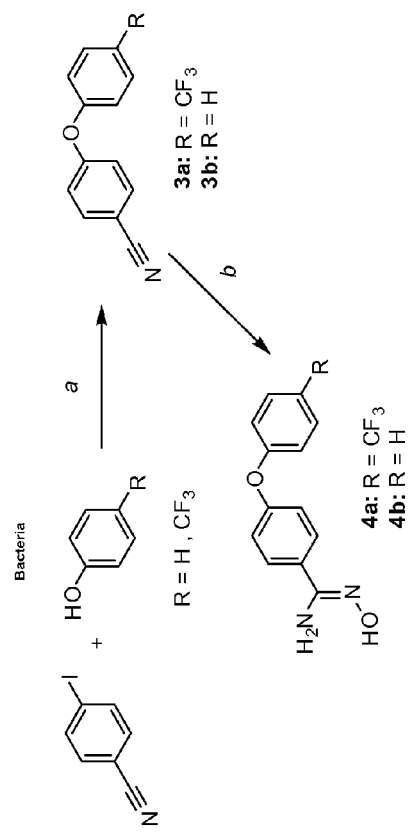
FIGS. 2 and 3 illustrate the schemes for synthesis of various compounds in accordance with various embodiments of the present invention.

In embodiments, the exemplary compounds described above may be synthesized according to the following general procedures. Both compound 1 and compound 2 follow the same synthesis up to the formation of hydroxyamidine. As illustrated in FIG. 2, initial coupling of commercially available starting materials of 4-iodobenzonitrile with either phenol or 4-trifluoromethyl phenol gave compounds 3a or 3b using standard Ullmann conditions. The purified product was then reacted with hydroxylamine to form the hydroxyamidine (compounds 4a or 4b) in quantitative yield.

Figure 3:
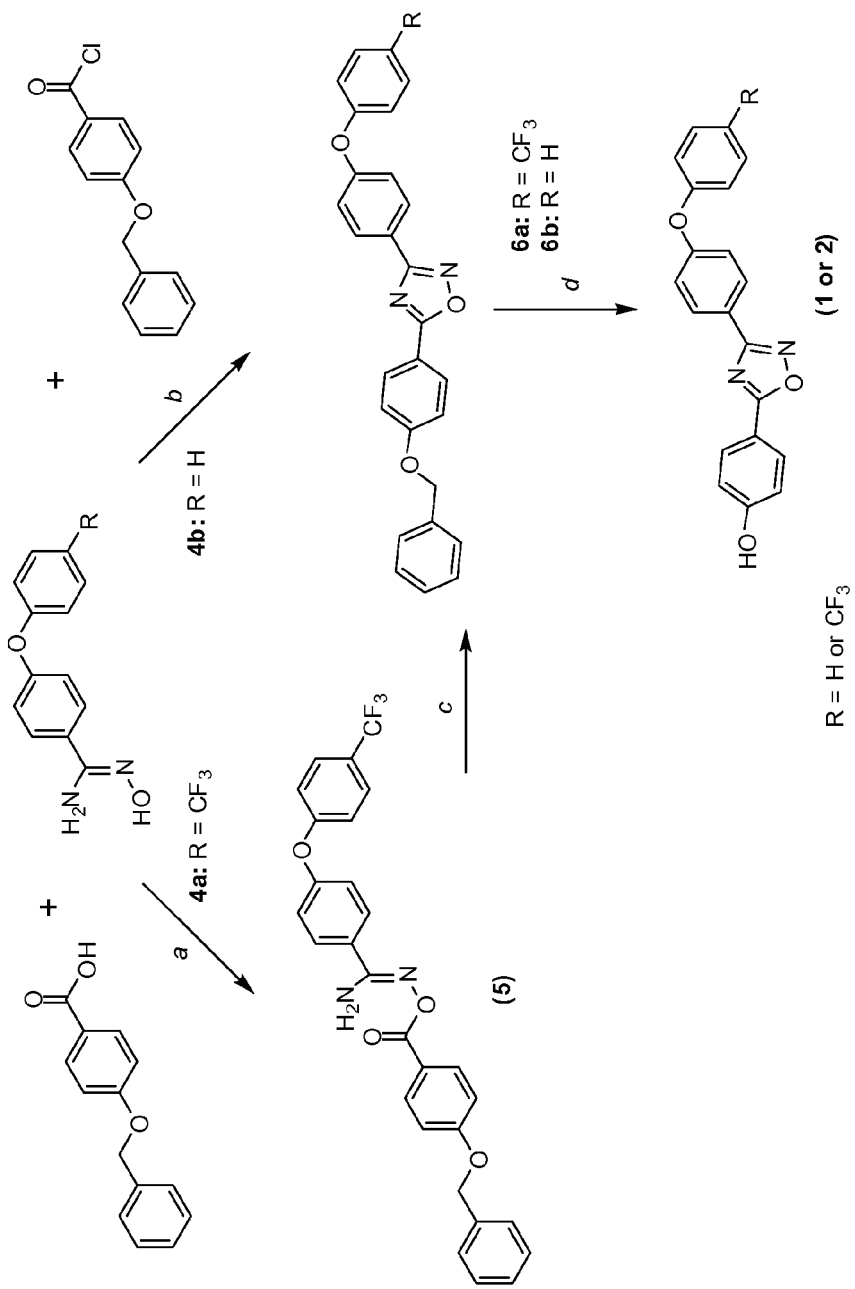

Trifluoromethyl hydroxyamidine (compound 4a) was coupled to 4-benzyloxybenzoylchloride using ethyldiisopropylamine to form the amidoxime intermediate (compound 5) in 58% yield (see FIG. 3) and was ring closed to form the 1,2,4-oxadiazole (compound 6a) with tetrabutyl-ammonium fluoride. Standard deprotection of compound 6a with Pd/C produced compound 1. Synthesis of compound 2 was achieved by following standard EDC coupling to compound 4b and commercially available 4-benzyloxybenzoic acid and then ring closing in a one pot reaction to give 1,2,4-oxadiazole (compound 6b). Deprotection of compound 6b using Pd/C provided compound 2 in 31% yield. More specific details regarding the synthesis steps outlined are provided below.

4-(4-(trifluoromethyl)phenoxy)benzonitrile (compound 3a—FIG. 2): To dried trifluoro-p-cresol (531 mg, 3.27 mmol), copper(I) iodide (83 mg, 0.4 mmol), cesium carbonate (1.42 g, 4.36 mmol), 4-iodobenzonitrile (500 mg, 2.18 mmol) and N,N-dimethylglycine hydrochloride (91 mg, 0.65 mmol) under nitrogen was added degassed 1,4-dioxane (10.0 mL). The whole mixture was heated at 90° C. for 140 hours. The cooled mixture was partitioned between ethyl acetate (50 mL) and water (50 mL). The organic layer was separated and the aqueous layer was extracted with ethyl acetate (2×50 mL). The organic layers were combined and washed with brine (100 mL) and dried with $Na_2SO_4$ and concentrated in vacuo. The crude liquid was placed on a silica gel column and purified $CH_2Cl_2$/Hex (1:8→1:4) and then was recrystallized with hot hexane to give the product as white crystals (286 mg, 50%). $^1$H NMR (500 MHz, $CDCL_3$) δ(ppm): 7.08 (1H, d, J=8.4 Hz), 7.15 (1H, d, J=8.8 Hz), 7.66 (1H, d, J=8.4 Hz), 7.67 (1H, d, J=8.8 Hz). $^{13}$C NMR (125 MHz, $CDCL_3$) δ(ppm): 107.4, 118.7, 119.1 (CH), 120.0 (CH), 122.9, 125.1, 127.0 (1C, q, J=32.5 Hz), 127.3, 127.8 (2CH, q, J=3.8 Hz), 134.5 (CH), 158.2, 160.4. $^{19}$F (282 MHz, $CDCL_3$) δ(ppm): −62.05 (3F, s). MS ($FAB^+$): 264 ($MH^+$). HRMS for $C_{14}H_8F_3NO$ ($MH^+$): calculated: 264.0636; found 264.0621.

(Z)-4-(4-(trifluoromethyl)phenoxy)-N'-hydroxy-benzamidine (compound 4a—FIG. 2): In ethanol (10.0 mL), was combined 4-(4-(trifluoromethyl)-phenoxy)benzonitrile (179 mg, 0.68 mmol) and hydroxylamine (167 μL, 2.72 mmol). The mixture was refluxed for 1 hour and then the reaction was cooled to room temperature and concentrated in vacuo to give the product (quantitative yield) which was taken to the next step without further purification. $^1$H NMR (500 MHz, $CDCL_3$) δ(ppm): 4.94 (3H, bs), 7.04-7.08 (4H, m), 7.60 (2H, d, J=9.0 Hz), 7.64 (2H, d, J=8.8 Hz). $^{13}$C NMR (125 MHz, $CDCL_3$) δ(ppm): 118.6 (CH), 119.7 (CH), 125 (1C, q, J=32.5 Hz), 127.4 (2CH, q, J=3.8 Hz), 127.7 (CH), 127.9 (CH), 128.6, 138.0, 152.3, 157.6. MS ($FAB^+$): 297 ($MH^+$). HRMS for $C_{14}H_{11}F_3N_2O_2$ ($MH^+$): calculated: 297.0851; found 297.0863.

(Z)-4-(4-(trifluoromethyl)phenoxy)-O-(4-(4-(benzyloxy)-benzoyl)benzamidoxime (compound 5-FIG. 3): To crude (Z)-4-(4-(trifluoromethyl)phenoxy)-N'-hydroxy-benzamidine (343 mg, 1.16 mmol) was added methylene chloride (10.0 mL) and N-ethyldiisopropylamine (303 mg, 2.32). The solution was cooled to 0° C. and placed under nitrogen. Then 4-benzyloxybenzoyl chloride (429 mg, 1.74 mmol) in methylene chloride (5.5 mL) was added dropwise and the mixture was stirred for 1 hour at 0° C. The solution was allowed to warm to room temperature and was then stirred for 24 hours. Ethylacetate (25 mL) was poured into the mixture and the solution was washed with water (25 mL) and then brine (25 mL). The organic layer was then dried with $MgSO_4$ and concentrated in vacuo. The material was purified using column chromatography EtOAc/Hex (1:3→4:1) and to give the product as crystals (343 mg, 58%).

5-(4-(benzyloxy)phenyl)-3-(4-phenoxyphenyl)-1,2,4-oxadiazole (compound 6a—FIG. 3): (Z)-4-(4-(trifluoromethyl)phenoxy)-O-(4-(benzyloxy)benzoyl)benzamidoxime (128 mg, 254 mmol) was placed under nitrogen and THF (6.0 mL) was added. Then tetrabutylammonium fluoride (1.0 M, 255 μL) was added dropwise and the solution was stirred at room temperature for 24 hours. The product was purified by column chromatography EtOAc/Hex (1:4) and was crystallized from hexane to give a white crystalline material (106 mg, 86%). $^1$H NMR (500 MHz, $CDCL_3$) δ(ppm): 7.17 (2H, s), 7.11-7.17 (6H, m), 7.36-7.47 (5H, m), 7.63 (2H, d, J=8.4 Hz), 8.17 (4H, t, J=9.0 Hz). $^{13}$C NMR (125 MHz, $CDCL_3$) δ(ppm): 70.4 ($CH_2$), 115.6 (CH), 117.2, 118.9 (CH), 119.8 (CH), 123.3, 125.9 (C, q, J=32.5 Hz), 127.5 (CH, q, J=4.1 Hz), 127.7 (CH), 128.5, 128.9, 129.7 (CH), 130.3 (CH), 136.2, 158.6, 162.6, 168.4, 175.8. $^{19}$F (282 MHz, $CDCL_3$) δ(ppm): −61.9 (3F, s). MS ($FAB^+$): 489 ($MH^+$). HRMS for $C_{28}H_{19}F_3N_2O_3$ ($MH^+$): calculated: 489.1426; found 489.1402.

4-(3-(4-(4-(trifluoromethyl)phenoxy)phenyl)-1,2,4-oxadiazol-5-yl)phenol (compound 1-FIG. 3): To 5-(4-(benzyloxy)phenyl)-3-(4-phenoxyphenyl)-1,2,4-oxadiazole (106 mg, 216 μmol) was added 10% Pd/C (7 mg, 7 μmol) and the mixture was suspended in methanol (3.0 mL) and THF (3.0 mL). The whole was stirred under $H_2$ at 55° C. for 24 hours. The solution was filtered through Celite and the solvent was removed under reduced pressure and then purified by column chromatography EtOAc/Hex (1:6→1:4) to give the product as a white solid (37 mg, 43%). $^1$H NMR (500 MHz, $CDCL_3$) δ(ppm): 5.38 (2H, bs), 6.99 (2H, d, J=8.6 Hz), 7.13 (2H, d, J=8.8 Hz), 7.15 (2H, d, J=8.6 Hz), 7.63 (2H, d, J=8.6 Hz), 8.13 (2H, d, J=8.6 Hz), 8.18 (2H, d, J=8.6 Hz). $^{13}$C NMR (125 MHz, $CDCL_3$) δ(ppm): 116.4 (CH), 116.9, 119.0 (CH), 119.8 (CH), 123.0, 125.3, 126.0 (C, q, J=32.5 Hz), 127.5 (CH, J=3.8 Hz), 129.7 (CH), 130.6, 158.7, 159.6, 160.1, 168.3, 175.9. $^{19}$F (282 MHz, $CDCL_3$) δ(ppm): −61.9 (3F, s). MS ($FAB^+$): 399 ($MH^+$). HRMS for $C_{21}H_{13}F_3N_2O_3$ ($MH^+$): calculated: 399.0957; found 399.0928.

4-phenoxybenzonitrile (compound 3b —FIG. 2): To phenol (1.23 g, 13.10 mmol), copper(I) iodide (333 mg, 1.75 mmol), cesium carbonate (5.69 g, 17.47 mmol), 4-iodobenzonitrile (2.00 g, 8.73 mmol) and N,N-dimethylglycine hydrochloride (366 mg, 2.62 mmol) under nitrogen was added degassed 1,4-dioxane (10.0 mL). The whole mixture was heated at 90° C. for 88 hours. The cooled mixture was partitioned between ethyl acetate (100 mL) and water (100 mL). The organic layer was separated and the aqueous layer was extracted with ethyl acetate (2×100 mL). The organic layers were combined and washed with brine (100 mL) and dried with $Na_2SO_4$ and concentrated in vacuo. The crude material was purified by column chromatography EtOAc/Hex (1:12→1:8) to give the pure product as a white solid (quantitative yield). $^1$H NMR (300 MHz, $CDCL_3$) δ(ppm): 7.00 (2H, d, J=9.1 Hz), 7.06 (2H, d, J=7.6 Hz), 7.23 (1H, t, J=7.2Hz), 7.41 (2H, t, J=8.1 Hz), 7.59 (2H, d, J=9.1 Hz). $^{13}$C NMR (75 MHz, $CDCL_3$) δ(ppm): 105.9, 118.0 (CH), 119.0, 120.5 (CH), 125.3 (CH), 130.4 (CH), 134.2 (CH), 154.9, 161.8. MS ($FAB^+$): 196 ($MH^+$). HRMS for $C_{13}H_9NO$ ($MH^+$): calculated: 196.0762; found 196.0780.

(Z)-N'-hydroxy-4-phenoxybenzamidine (compound 4b —FIG. 2): In ethanol (5.0 mL), was combined 4-phenoxybenzonitrile (200 mg, 1.02 mmol) and hydroxylamine (250 μL, 4.09 mmol). The mixture was refluxed for 3 hours. The reaction was cooled and then concentrated in vacuo to give the product, which was taken to the next step without further purification (quantitative yield). $^1$H NMR (500 MHz, $CDCL_3$) δ(ppm): 4.87 (2H, bs), 7.01 (2H, d, J=9.0 Hz), 7.03 (2H, dd, J=8.7, 1.1 Hz), 7.15 (2H, tt, J=7.4, 1.1 Hz), 7.36 (2H, dd, J=8.6, 7.3 Hz), 7.59 (2H, d, J=9.0 Hz). $^{13}$C NMR (125 MHz, $CDCL_3$) δ(ppm): 118.6 (CH), 119.6 (CH), 124, 127.3, 127.6 (CH), 130.1 (CH), 152.5, 156.6, 159.3. MS ($FAB^+$): 229 ($MH^+$). HRMS for $C_{13}H_{12}N_2O_2$ ($MH^+$): calculated: 229.0977; found 229.0977.

5-(4-(benzyloxy)phenyl)-3-(4-phenoxyphenyl)-1,2,4-oxadiazole (compound 6b —FIG. 3): To a solution of 4-benzyloxybenzoic acid (152 mg, 665 μmol) and benzylhydroxyamidine (152 mg, 665 μmol) in methylene chloride (10.0 mL) was added EDC (135 mg, 698 μmol) in methylene chloride (5.0 mL). The mixture was stirred for 5 hours. Then tetrabutylammonium fluoride (1.0 M in THF, 1.33 mL) was added dropwise and the solution was stirred at room temperature for 28.5 hours. An additional (191 mg, 996 mmol) of EDC was added and the solution was stirred for 23 hours then an additional amount of tetrabutylammonium fluoride (1.0 M in THF, 1.33 mL) was added and the solution was stirred for 25 hours. The product was purified by column chromatography EtOAc/Hex (1:4→1:2) and was crystallized from ethylacetate/hexane (1:1) to give a white crystalline material (75 mg, 27%). $^1$H NMR (500 MHz, $CDCL_3$) δ(ppm): 5.15 (2H, s), 7.07-7.12 (6H, m), 7.17 (1H, t, J=7.4 Hz) 7.34-7.46 (7H, m), 8.12 (2H, d, J=9.0 Hz), 8.15 (2H, d, J=8.4 Hz). $^{13}$C NMR (125 MHz, $CDCL_3$) δ(ppm): 70.4 ($CH_2$), 115.5 (CH), 117.3, 118.6 (CH), 119.9 (CH), 121.9, 124.3 (CH), 127.7 (CH), 128.5 (CH), 128.9 (CH), 129.4 (CH), 130.2 (CH), 130.3 (CH), 136.3, 156.4, 160.2, 162.5, 168.5, 175.6. MS ($FAB^+$): 421 ($MH^+$). HRMS for $C_{27}H_{20}F_3N_2O_3$ ($MH^+$): calculated: 421.1552; found 421.1540.

4-(3-(4-phenoxyphenyl)-1,2,4-oxadiazol-5-yl)phenol (compound 2-FIG. 3): To 5-(4-(benzyloxy)phenyl)-3-(4-phenoxyphenyl)-1,2,4-oxadiazole (50 mg, 120 μmol) was added 10% Pd/C (1 mg, 8 μmol) and the mixture was suspended in methanol (3.0 mL) and THF (3.0 mL). The solution was stirred under $H_2$ at 55° C. for 24 hours. The solution was filtered through Celite and the solvent was removed under reduced pressure and then purified by column chromatography EtOAc/Hex (1:6→1:4) to give the product as a white solid (12 mg, 31%). $^1$H NMR (500 MHz, $CDCL_3$) δ(ppm): 5.83 (1H, bs), 6.98 (2H, d, J=8.2 Hz), 7.09 (4H, m), 7.18 (1H, t, J=7.6 Hz), 8.12 (2H, t, J=7.7 Hz), 8.12 (2H, d, J=6.8 Hz). $^{13}$C NMR (125 MHz, $CDCL_3$) δ(ppm): 116.3 (CH), 117.2, 118.6 (CH), 119.9 (CH), 121.8, 124.4 (CH), 129.5 (CH), 130.2 (CH), 130.6 (CH), 156.4, 159.8, 160.3, 168.5, 175.7. MS ($FAB^+$): 331 ($MH^+$). HRMS for $C_{20}H_{14}N_2O_3$ ($MH^+$): calculated: 331.1083; found 331.1056.

(Z)-4-(4-(trifluoromethyl)phenoxy)-N'-hydroxybenzamidine (compound 7-structure shown below): In a one neck round bottom flask, (Z)-4-(4-(Trifluoromethyl)phenoxy)-N'-hydroxybenzamidine (53 mg, 0.18 mmol) was placed under nitrogen and dissolved in methylene chloride (3.0 mL). N-ethyldiisopropylamine (62 μL, 0.26 mmol) was added and the solution was cooled to 0° C. Acetyl chloride (62 μL, 0.36 mmol) was added dropwise and the mixture was stirred for 1 hour at 0° C. The solution was allowed to warm to room temperature and was then stirred for an additional 19 hours. Ethyl acetate was poured into the mixture and the solution was washed with water (25 mL) and then brine (25 mL). The organic layer was then dried with $MgSO_4$ and concentrated in vacuo. The crude solid was purified using silica gel column chromatography (EtOAc/Hex 1:8 to 1:2) and recrystallized from ethyl ether to give the product as a white powder (41 mg, 67%). $^1$H NMR (500 MHz, $CDCL_3$) δ(ppm): 5.09 (2H, bs), 7.08 (4H, dd, J=8.8, 2.59 Hz), 7.61 (2H, d, J=8.6 Hz), 7.73 (2H, d, J=8.6 Hz). $^{13}$C NMR (125 MHz, $CDCL_3$) δ(ppm): 20.2 ($CH_3$), 118.8 (CH), 119.8 (CH), 125.3, 125.9 (1C, q, J=32.7 Hz), 127.2, 127.4 (2CH, q, J=3.9 Hz), 128.9 (CH), 155.6, 158.6, 159.7, 169.0. $^{19}$F (282 MHz, $CDCL_3$) δ(ppm): −61.89 (3F, s). MS ($FAB^+$): 339 ($MH^+$). HRMS for $C_{16}H_{13}F_3N_2O_3$ ($MH^+$): calculated: 339.0957; found 339.0938.

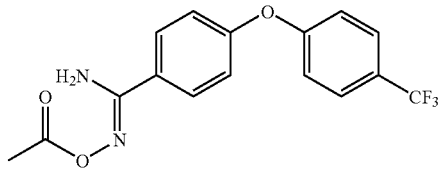 [SMILES: CC(=O)O/N=C(\N)c1ccc(Oc2ccc(C(F)(F)F)cc2)cc1]

3-(4-(4-(trifluoromethyl)phenoxy)phenyl)-5-methyl-1,2,4-oxadiazole (compound 8-structure shown below): (Z)-4-(4-(Trifluoromethyl)phenoxy)-N'-hydroxybenzamidine (79 mg, 0.23 mmol) was placed under nitrogen and THF was added. Then tetrabutylammonium fluoride (67 μL, 0.23 mmol) was added dropwise and the solution was stirred at room temperature for 92 hours 40 minutes. The product was purified by column chromatography over silica gel (EtOAc/Hex 1:12) to give a white solid (9.0 mg, 12%). $^1$H NMR (500 MHz, $CDCL_3$) δ(ppm): 2.66 (3H, s), 7.11-7.14 (4H, m), 7.62 (2H, d, J=8.4 Hz), 8.08 (2H, d, J=9.0 Hz). $^{13}$C NMR (125 MHz, $CDCL_3$) δ(ppm): 12.61 ($CH_3$), 119.0 (CH), 119.7 (CH), 122.9, 125.3, 126.0 (C, q, J=32.5 Hz), 127.5 (CH, q, J=3.8 Hz), 129.6 (CH), 158.7, 159.6, 167.9, 176.8. $^{19}$F (282 MHz, $CDCL_3$) δ(ppm): −61.89 (3F, s). MS ($FAB^+$): 321 ($MH^+$). HRMS for $C_{16}H_{11}F_3N_2O_2$ ($MH^+$): calculated: 320.0773; found 320.0779.

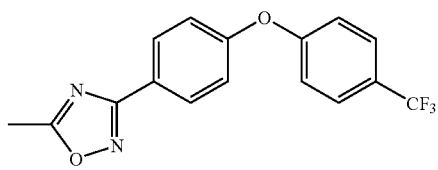 [SMILES: Cc1nc(-c2ccc(Oc3ccc(C(F)(F)F)cc3)cc2)no1]

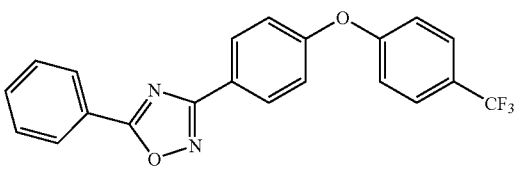

(Z)-4-(4-(trifluoromethyl)phenoxy)-O-benzoylbenzamidoxime (compound 9-structure shown below): (Z)-4-(4-(Trifluoromethyl)phenoxy)-N'-hydroxy-benzamidine (300 mg, 1.01 mmol) was added to methylene chloride (10.0 mL) and N-ethyldiisopropylamine (353 μL, 2.03 mmol). The solution was cooled to 0° C. and placed under nitrogen. Then benzoyl chloride (176 μL, 1.52 mmol) was added dropwise and the mixture was stirred for 2 hours at 0° C. The solution was allowed to warm to room temperature and was then stirred for 14 hours. Ethyl acetate (40 mL) was poured into the mixture and the solution was washed with water (2×40 mL) and then brine (40 mL). The organic layer was then dried with $MgSO_4$ and concentrated in vacuo. The solid residue was purified using column chromatography over silica gel (EtOAc/Hex 1:4 to 1:1.5) to give the product as white crystals (368 mg, 91%). $^1$H NMR (500 MHz, $CDCL_3$) δ(ppm): 5.30 (2H, bs), 7.07-7.11 (4H, m), 7.47-7.52 (3H, m), 7.59-7.62 (3H, m), 7.80 (2H, t, J=9.0 Hz), 8.10 (2H, t, J=10.0 Hz) $^{13}$C NMR (125 MHz, $CDCL_3$) δ(ppm): 118.8 (CH), 119.8 (CH), 125.5 (C, q, J=32.8 Hz), 127.2, 127.5 (CH, q, J=3.6 Hz), 128.6, 128.8 (CH), 129.1 (CH), 129.7 (CH), 133.3 (CH), 138.2, 156.7, 158.7, 159.7, 164.2.

(Z)-4-(4-(Trifluoromethyl)phenoxy)-O-(4-(4-fluorobenzoyl)benzamidoxime (compound 11-structure shown below): A solution of (Z)-4-(4-(trifluoromethyl)phenoxy)-N'-hydroxy-benzamidine (130 mg, 0.38 mmol) in methylene chloride (1.5 mL) and N-ethyldiisopropylamine (133 μL, 0.76 μmol) was cooled in an iced-water bath under an atmosphere of nitrogen. A solution of 4-fluorobenzoyl chloride (60 μL, 0.51 mmol) was added dropwise to the previous solution and the mixture was stirred for 1 hour at iced-water temperature. The solution was allowed to warm to room temperature and was then stirred for 24 hours. Ethyl acetate (25 ml) was poured into the mixture and the solution was washed with aq. $NaHCO_3$ (25 ml) water (25 ml) and then brine (25 ml). The organic layer was then dried over anhydrous $MgSO_4$ and was concentrated to dryness in vacuo. The solid residue was purified using column chromatography on silica gel (EtOAc/Hex, 1:3 to 4:1) to give the product as a white solid (172 mg, 94%). $^1$H NMR (500 MHz, $CDCL_3$) δ(ppm): 5.18 (bs), 7.07-7.11 (4H, m), 7.16 (2H, t, J=8.7 Hz), 7.62 (2H, d, J=8.4 Hz), 7.79 (2H, d, J=9.0 Hz) 8.12 (2H, dd, J=9.0, 5.4 Hz). $^{19}$F (282 MHz, $CDCL_3$) δ(ppm): ⁻61.89 (3F, s), ⁻105.03-⁻105.13 (1F, m). MS (FAB⁺): 419 (MH⁺). HRMS for $C_{21}H_{14}F_4N_2O_3$ (MH⁺): calculated: 419.1019; found 419.1031.

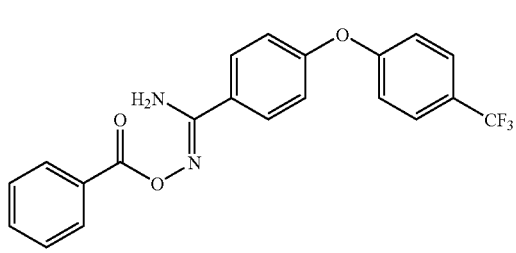 [SMILES: N/C(=N\OC(=O)c1ccccc1)c1ccc(Oc2ccc(C(F)(F)F)cc2)cc1]

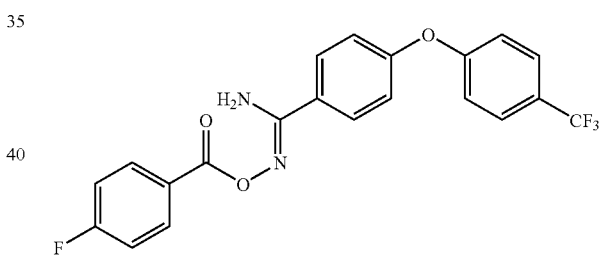

3-(4-(4-(trifluoromethyl)phenoxy)phenyl)-5-phenyl-1,2,4-oxadiazole (compound 10-structure shown below): (Z)-4-(4-(trifluoromethyl)phenoxy)-N'-(O-benzoyl)hydroxybenzamidine (96 mg, 240 mmol) was placed under nitrogen and THF (10.0 mL) was added. Then tetrabutylammonium fluoride (69 μL, 240 mmol) was added dropwise and the solution was stirred at room temperature for 15 hours. The solvent was removed under reduced pressure and the crude solid was purified by column chromatography over silica gel (EtOAc/Hex 1:2 to 1:1) and was crystallized from hot hexane to give the product as a white solid (91 mg, 100%) yield. $^1$H NMR (500 MHz, $CDCL_3$) δ(ppm): 7.14 (2H, dd, J=9.0, 0.8 Hz), 7.17 (2H, d, J=9.0 Hz), 7.55-7.59 (2H, m), 7.61-7.65 (3H, m), 8.20 (2H, d, J=9.0 Hz), 8.22-8.24 (2H, m). $^{13}$C NMR (125 MHz, $CDCL_3$) δ(ppm): 119.0 (CH), 119.8 (CH), 123.1, 124.4, 125.4, 126.2 (C, q, J=32.8 Hz), 127.5 (CH, q, J=3.8 Hz), 128.4 (CH), 129.4 (CH), 129.8 (CH), 133.0 (CH), 158.8, 159.6, 168.5, 176.0. $^{19}$F (282 MHz, $CDCL_3$) δ(ppm): ⁻61.9 (3F, s). MS (FAB⁺): 382 (MH⁺). HRMS for $C_{21}H_{13}F_3N_2O_2$ (MH⁺): calculated: 383.1007; found 383.0982.

(Z)-4-(4-(trifluoromethyl)phenoxy)-O-(4-bromobenzoyl)benzamidoxime (compound 12-structure shown below): (Z)-4-(4-(trifluoromethyl)phenoxy)-N'-hydroxybenzamidine (200 mg, 675 mmol) was added to methylene chloride (5.0 mL) and N-ethyldiisopropylamine (238 μL, 1.35 mmol). The solution was cooled to 0° C. and placed under nitrogen. Then 4-bromobenzoyl chloride (151 mg, 0.67 mmol) was added dropwise and the mixture was stirred for 1 hour at 0 C. The solution was allowed to warm to room temperature and was then stirred for 12 hours. Ethyl acetate (40 ml) was poured into the mixture and the solution was washed with water (40 ml) and then brine (40 ml). The organic layer was then dried with $MgSO_4$ and concentrated in vacuo. The solid residue was purified using column chromatography over silica gel (EtOAc/Hex 1:10 to 1:1) to give the product as white crystals (302 mg, 93%). $^1$H NMR (300 MHz, DMSO-$d_6$) δ(ppm): 7.05 (2H, bs), 7.22 (4H, d, J=8.8 Hz), 7.76 (4H, t, J=8.4 Hz), 8.85 (2H, d, J=8.6 Hz), 8.14 (2H, d, J=8.6 Hz). $^{13}$C NMR (125 MHz, DMSO-$d_6$) δ(ppm): 118.6 (CH), 119.4 (CH), 127.2, 124.5 (C, q, J=32.6 Hz), 127.6 (CH, q, J=3.3 Hz), 127.8, 128.6, 128.9, 129.2 (CH), 131.6 (CH), 131.7 (CH), 156.4, 157.1, 159.7, 162.9. $^{19}$F (282 MHz, $CDCL_3$) δ(ppm): ⁻60.6

(3F, s). MS (FAB+): 479 (MH+). HRMS for $C_{21}H_{14}BrF_3N_2O_3$ (MH+): calculated: 479.0218; found 479.0211.

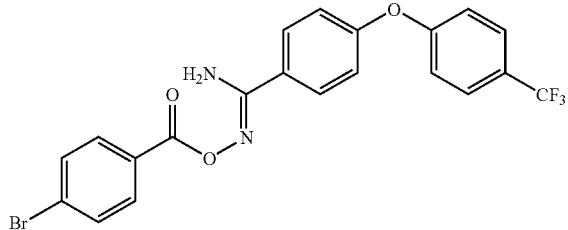 [SMILES: N/C(=N\OC(=O)c1ccc(Br)cc1)c1ccc(Oc2ccc(C(F)(F)F)cc2)cc1]

3-(4-(4-(trifluoromethyl)phenoxy)phenyl)-5-(4-bromophenyl-1,2,4-oxadiazole (compound 13-structure shown below): (Z)-4-(4-(trifluoromethyl)phenoxy)-N'-(4-bromobenzoyl)benzamidoxime (176.4 mg 368.1 mmol) was placed under nitrogen and THF (10.0) was added. Then tetrabutylammonium fluoride (107 μL, 368 mmol) was added dropwise and the solution was stirred at room temperature for 22 hours. The solvent was removed under reduced pressure. The solid was purified by column chromatography over silica gel (EtOAc/Hex 1:2 to 1:1) and was crystallized from hot hexane to give a white crystalline material (164, 96%). $^1$H NMR (500 MHz, CDCL$_3$) δ(ppm): 7.13-7.17 (4H, m), 7.63 (2H, d, J=8.4 Hz), 7.70 (2H, d, J=8.8 Hz), 8.07 (2H, d, J=8.8 Hz), 8.17 (2H, d, J=8.8 Hz). $^{13}$C NMR (125 MHz, CDCL$_3$) δ(ppm): 119.0 (CH), 119.7 (CH), 122.8, 123.3, 125.3, 126.0 (C, q, J=32.5 Hz), 127.5 (CH, q, J=3.8 Hz), 128.0, 129.7 (CH), 158.8, 159.5, 168.6, 175.1. $^{19}$F (282 MHz, CDCL$_3$) δ(ppm): −61.9 (3F, s). MS (FAB+): 461 (MH+). HRMS for $C_{21}H_{12}BrF_3N_2O_2$ (MH+): calculated: 461.0112; found 461.0137.

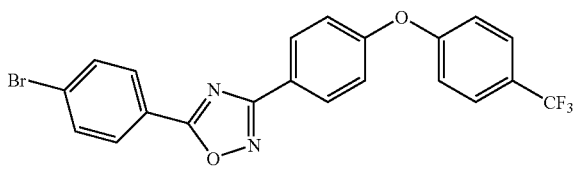 [SMILES: FC(F)(F)c1ccc(Oc2ccc(-c3noc(-c4ccc(Br)cc4)n3)cc2)cc1]

(Z)-4-(4-(trifluoromethyl)phenoxy)-O-(4-nitrobenzoyl)benzamidoxime (compound 14-structure shown below): In a one neck round bottom flask, (Z)-4-(4-(Trifluoromethyl)phenoxy)-N'-hydroxybenzamidine (826 mg, 2.79 mmol) was placed under nitrogen and dissolved in methylene chloride (15.0 mL). N-ethyldiisopropylamine (980 μL, 5.57 mmol) was added and the solution was cooled to 0° C. Then 4-nitrobenzoyl chloride (792 mg, 4.18 mmol) in methylene chloride (10 mL) was added dropwise and the mixture was stirred for 1 hour at 0° C. The solution was allowed to warm to room temperature and was then stirred for 24 hours. Then ethyl acetate (50 mL) was poured into the mixture and the solution was washed with water (50 mL) and then brine (50 mL). The organic layer was then dried with MgSO$_4$ and concentrated in vacuo. The material was purified using column chromatography (EtOAc/Hex 1:3 to 4:1) and to give the product (1.20 g, 97%) as yellow crystals. $^1$H NMR (500 MHz, CDCL$_3$) δ(ppm): 5.18 (2H, bs), 7.09 (2H, d, J=8.4 Hz), 7.12 (2H, d, J=8.8 Hz), 7.63 (2H, d, J=8.6 Hz), 7.79 (2H, d, J=8.8 Hz), 8.28 (2H, d, J=8.9 Hz), 8.34 (2H, d, J=9.0 Hz). $^{13}$C NMR (125 MHz, CDCL$_3$) δ(ppm): 118.9 (CH), 119.8 (CH), 124.0 (CH), 126.1 (C, q, J=32.9 Hz), 126.7, 127.6 (CH, q, J=3.8 Hz), 129.1 (CH), 129.4, 129.8, 130.8 (CH), 135.2, 150.8, 157.2, 159.0, 162.4. $^{19}$F (282 MHz, CDCL$_3$) δ(ppm): −61.9 (3F, s). MS (FAB+): 446 (MH+). HRMS for $C_{21}H_{14}F_3N_3O_5$ (MH+): calculated: 445.0886; found 445.0894.

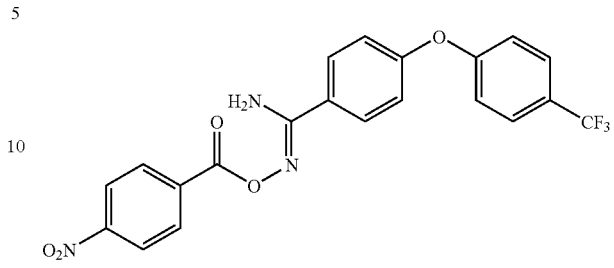

3-(4-(4-(trifluoromethyl)phenoxy)phenyl)-5-(4-nitrophenyl-1,2,4-oxadiazole (compound 15-structure shown below): (Z)-4-(4-(trifluoromethyl)phenoxy)-O-(4-bromobenzoyl)benzamidoxime (569 mg, 1.27 mmol) was placed under nitrogen and THF (30 mL) was added. Then tetrabutylammonium fluoride (1.0 M, 1.30 μL) was added dropwise the solution was stirred at room temperature for 1 hour. The solvent was removed under reduced pressure and the product was purified by column chromatography over silica gel (EtOAc/Hex 1:6) and was crystallized from hot hexane to give a yellow solid (430 mg, 79%). $^1$H NMR (500 MHz, CDCL$_3$) δ(ppm): 7.15 (2H, dd, J=9.1, 0.7 Hz), 7.18 (2H, d, J=8.8 Hz), 7.65 (2H, dd, J=9.1, 0.7 Hz), 8.20 (2H, d, J=9.0 Hz), 8.43 (4H, s). $^{13}$C NMR (125 MHz, CDCL$_3$) δ(ppm): 119.2 (CH), 119.8 (CH), 122.3, 124.6 (CH), 126.1 (C, q, J=32.5 Hz), 127.6 (CH, q, J=3.8 Hz), 129.4 (CH), 129.7, 129.8, 150.4, 159.4, 169.0, 173.9. $^{19}$F (282 MHz, CDCL$_3$) δ(ppm): −61.9 (3F, s). MS (FAB+): 427 (MH+). HRMS for $C_{21}H_{12}F_3N_3O_4$ (MH+): calculated: 427.0780; found 427.0782.

4-(3-(4-(4-(trifluoromethyl)phenoxy)phenyl)-1,2,4-oxadiazol-5-yl)aniline (compound 16-structure shown below): Iron powder (132 mg, 2.33 mmol), water (210 μL, 11.8 mmol) and 12 N HCl (10 μL, 0.11 mmol) were added consecutively to a solution of the 3-(4-(4-(trifluoromethyl)phenoxy)phenyl)-5-(4-nitrophenyl-1,2,4-oxadiazole (46 mg, 0.11 mmol) in ethanol (6.0 mL). The mixture was heated at 95 C for 1 hours. The mixture was filtered while still hot and then washed with additional ethanol (10 mL). The filtrates were combined and the solvent was removed in vacuo. The crude solid product was purified by silica gel column chromatography (EtOAc/Hex 1:8) to give the product (31 mg, 72%) as a white solid. $^1$H NMR (500 MHz, CDCL$_3$) δ(ppm): 6.35 (2H, bs) 6.99 (2H, d, J=8.8 Hz), 7.13 (2H, d, J=8.2 Hz), 7.15 (2H, d, J=8.8 Hz), 7.63 (2H, d, J=8.6 Hz), 8.11 (2H, d, J=8.8 Hz), 8.17 (2H, d, J=8.8 Hz). $^{13}$C NMR (125 MHz, CDCL$_3$) δ(ppm): 114.0, 114.7 (CH), 118.9 (CH), 119.8 (CH), 123.5, 125.4, 125.8 (C, q, J=32.5 Hz), 127.5 (CH, q, J=3.8 Hz), 129.7 (CH), 130.3 (CH), 150.9, 158.5, 159.8, 168.2, 176.3. $^{19}$F (282 MHz, CDCL$_3$) δ(ppm): −61.85 (3F, s). MS (FAB+): 398 (MH+). HRMS for $C_{21}H_{14}F_3N_3O_2$ (MH+): calculated: 397.1038; found 397.1036.

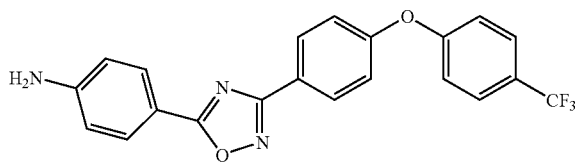 [SMILES: O=[N+]([O-])c1ccc(-c2nc(-c3ccc(Oc4ccc(C(F)(F)F)cc4)cc3)no2)cc1]

(Z)-N'-hydroxybenzamidine (compound 17-structure shown below): A solution of ethanol (5.0 mL), benzonitrile (203 mg, 1.97 mmol) and hydroxylamine (520 mg, 7.87 mmol) were refluxed for 1 hour. The reaction was then cooled to room temperature and concentrated in vacuo to give the a clear oil which was taken to the next step without further purification (268 mg, 100%). $^1$H NMR (500 MHz, CDCL$_3$) δ(ppm): 4.92 (2H, bs), 7.38-7.44 (3H, m), 7.62-7.65 (2H, m). $^{13}$C NMR (125 MHz, CDCL$_3$) δ(ppm): 126.1 (CH), 128.9 (CH), 130.2 (CH), 132.6, 152.8. MS (FAB$^+$): 137 (MH$^+$). HRMS for C$_7$H$_8$N$_2$O (MH$^+$): calculated: 137.0715; found 137.0718.

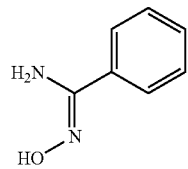

Benzyl-O-4-fluorobenzamidoxime (compound 18-structure shown below): A solution of (Z)-N'-hydroxybenzamidine (102 mg, 0.75 mmol) in methylene chloride (2.0 mL) and N-ethyldiisopropylamine (26 μL, 1.5 μmol) was cooled to 0° C. in an iced-water bath under an atmosphere of nitrogen. Then 4-fluorobenzoyl chloride (13 μL, 1.1 mmol) was added dropwise and the mixture was stirred for 1 hour at 0° C. The solution was allowed to warm to room temperature and was then stirred for 19 hours. Then ethyl acetate (20 mL) was poured into the mixture and the solution was washed with water (20 mL) and then brine (20 mL). The organic layer was then dried with MgSO$_4$ and concentrated in vacuo. The material was purified using silica gel column chromatography (EtOAc/Hex 1:8 to 2:1) to give the product (124 mg, 64%) as white crystals. (500 MHz, CDCL$_3$) δ(ppm): 5.15 (2H, bs), 7.16 (2H, t, J=8.7 Hz), 7.43-7.47 (2H, m), 7.49-7.53 (1H, m), 7.76-7.78 (2H, m), 8.12 (2H, dd, J=9.0, 5.4 Hz). $^{13}$C NMR (75 MHz, CDCL$_3$) δ(ppm): 116.0 (2CH, d, J=21.8 Hz), 126.1, 127.1 (CH), 129.0 (CH), 131.2, 131.4 (CH), 132.2 (2CH, d, J=9.5 Hz), 157.5, 163.3, 166.6 (C, d, J=254.3 Hz). $^{19}$F (282 MHz, CDCL$_3$) δ(ppm): ⁻105.2-⁻105.3 (1F, m). MS (FAB$^+$): 259 (MH$^+$). HRMS for C$_{14}$H$_{11}$FN$_2$O$_2$ (MH$^+$): calculated: 259.0883; found 259.0904.

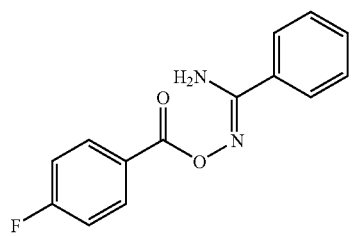 [SMILES: N/C(=N\OC(=O)c1ccc(F)cc1)c1ccccc1]

5-(4-fluorophenyl)-3-phenyl-1,2,4-oxadiazole (compound 19-structure shown below): Benzyl-O-(4-fluorobenzami-doxime (116 mg, 449 mmol) was placed under nitrogen and THF (5.0 mL) was added. Then tetrabutylammonium fluoride (1.0 M, 450 μL) was added dropwise the solution was stirred at room temperature for 21 hours. The solid residue was purified by column chromatography over silica gel (EtOAc/Hex 1:8) and the product was crystallized from hot hexane to give clear crystals (66 mg, 61%). $^1$H NMR (300 MHz, CDCL$_3$) δ(ppm): 7.23 (2H, t, J=8.3 Hz), 7.49-7.51 (3H, m), 8.16 (2H, dd, J=2.8, 6.9 Hz), 8.21 (2H, dd, J=5.4, 8.3 Hz). $^{13}$C NMR (75 MHz, CDCL$_3$) δ(ppm): 116.7 (2CH, d, J=21.8 Hz), 127.0, 127.7 (CH), 129.1 (CH), 130.8 (CH), 131.1 (2CH, d, J=54.0 Hz), 163.9, 167.3, 169.18, 175.0. MS (FAB$^+$): 241 (MH$^+$). HRMS for C$_{14}$H$_9$FN$_2$O (MH$^+$): calculated: 241.0777; found 241.0759.

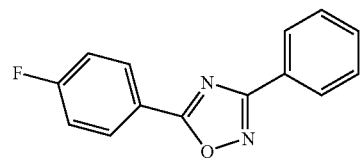 [SMILES: Fc1ccc(-c2nc(-c3ccccc3)no2)cc1]

Benzyl-O-4-bromobenzamidoxime (compound 20-structure shown below): (Z)-N'-Hydroxybenzamidine (226, 1.66 mmol) was added methylene chloride (5.0 mL) and N-ethyldiisopropylamine (433 mg, 3.32 mmol). The solution was cooled to 0° C. and placed under nitrogen. Then 4-bromobenzoyl chloride (372 mg, 1.66 mmol) was added dropwise and the mixture was stirred for 1 hour at 0° C. The solution was allowed to warm to room temperature and was then stirred for 48 hours. Ethyl acetate (25.0 mL) was poured into the mixture and the solution was washed with water (20 mL) and then brine (20 mL). The organic layer was then dried with MgSO$_4$ and concentrated in vacuo. The material was purified using column chromatography over silica gel (EtOAc/Hex 1:4 to 1:1) to give the product as white crystals (148 mg, 28%). (Used immediately in the next step) $^1$H NMR (500 MHz, DMSO-d$_6$) δ(ppm): 7.02 (2H, bs), 7.45-7.56 (3H, m), 7.74-7.77 (4H, m), 8.13 (2H, d, J=8.6 Hz). $^{13}$C NMR (125 MHz, DMSO-d$_6$) δ(ppm): 126.9 (CH), 127.1, 128.4 (CH), 128.6 (CH), 130.6, 131.5 (CH), 131.6 (CH), 131.7, 175.2. MS (FAB$^+$): 319 (MH$^+$). HRMS for C$_{14}$H$_{11}$BrN$_2$O$_2$ (MH$^+$): calculated: 319.0082; found 319.0085.

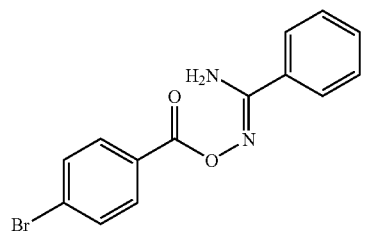 [SMILES: N/C(=N\OC(=O)c1ccc(Br)cc1)c1ccccc1]

5-(4-bromophenyl)-3-phenyl-1,2,4-oxadiazole (compound 21-structure shown below): Benzyl-O-4-bromobenzamidoxime (95 mg, 298 mmol) was placed under nitrogen and THF (10.0 mL) was added. Then tetrabutylammonium fluoride (1.0 M in THF, 85 μL) was added dropwise the solution was stirred at room temperature for 16 hours 30 minutes. The solvent was removed under reduced pressure and the solid residue was purified by column chromatography over silica gel (EtOAc/Hex 1:6) and to give a white crystalline material (76 mg, 84%). $^1$H NMR (500 MHz, CDCL$_3$) δ(ppm): 7.48-

7.52 (3H, m), 7.67 (2H, d, J=8.8 Hz), 8.06 (2H, d, J=8.8 Hz), 8.13-8.15 (2H, m). $^{13}$C NMR (125 MHz, CDCL$_3$) δ(ppm): 126.9, 127.7 (CH), 127.9, 129.0 (CH), 129.7 (CH), 131.5, 132.6, 169.2, 175.0. MS (FAB$^+$): 301 (MH$^+$). HRMS for C$_{14}$H$_9$BrN$_2$O (MH$^+$): calculated: 300.9976; found 300.9980.

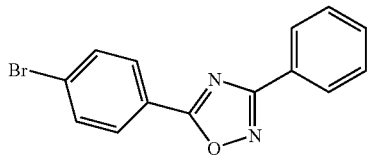 [SMILES: Brc1ccc(-c2nc(-c3ccccc3)no2)cc1]

5-(4-(benzyloxy)phenyl)-3-phenyl-1,2,4-oxadiazole (compound 22-structure shown below): EDC (299 mg, 1.54 mmol) in CH$_2$Cl$_2$ (5.0 mL) was added to a solution of 4-benzyloxybenzoic acid (336, 1.47 mmol) and benzylhydroxyamidine (200 mg, 1.47 mmol) in CH$_2$Cl$_2$ (5.0 mL). The mixture was stirred for 6 hours and checked by TLC for completion. Then tetrabutylammonium fluoride (1.0 M in THF, 2.95 mL) was added dropwise and the solution was stirred at room temperature for 12 hours. The solvent was removed under reduced pressure and the product was purified by column chromatography over silica gel (EtOAc/Hex (:4→1:2) and was crystallized from hot ethyl acetate to give a white crystalline material (107 mg, 22%). $^1$H NMR (500 MHz, CDCL$_3$) δ(ppm): 5.16 (2H, s), 7.11 (2H, d, J=8.8 Hz), 7.36-7.46 (5H, m), 7.49-7.51 (3H, m), 8.16 (4H, d, J=8.6 Hz). $^{13}$C NMR (125 MHz, CDCL$_3$) δ(ppm): 70.4 (CH$_2$), 115.5 (CH), 117.3, 127.3, 127.7 (CH), 127.8 (CH), 128.5 (CH), 128.9, 129.0 (CH), 130.3 (CH), 131.3, 136.2, 162.5, 169.0, 175.8. MS (FAB$^+$): 329 (MH$^+$). HRMS for C$_{21}$H$_{16}$N$_2$O$_2$ (MH$^+$): calculated: 329.1290; found 329.1302.

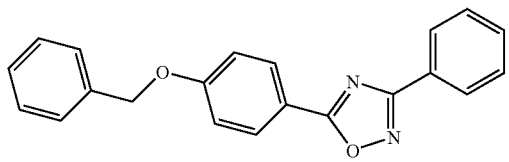 [SMILES: c1ccc(COc2ccc(-c3nc(-c4ccccc4)no3)cc2)cc1]

4-(3-Phenyl-[1,2,4]oxadiazol-5-yl)-phenol (compound 23-structure shown below): A suspension of 5-(4-(benzyloxy)phenyl)-3-phenyl-1,2,4-oxadiazole (90 mg, 0.27 mmol) and 10% Pd/C (2 mg, 7 μmol) in methanol (3.0 mL) and THF (3.0 mL) was stirred in a single necked round bottom flask fitted with a condenser under an atmosphere of hydrogen at 55° C. for 72 hours. The solution was filtered through Celite and the solvent was removed under reduced pressure and then purified by column chromatography (EtOAc/Hex 1:2) to give the product (7 mg, 11%) as a white solid. $^1$H NMR (500 MHz, CDCL$_3$) δ(ppm): 6.86 (2H, d, J=8.8 Hz), 6.99 (2H, d, J=9.2 Hz), 8.01 (2H, d, J=8.8 Hz), 8.05 (2H, d, J=9.2 Hz).

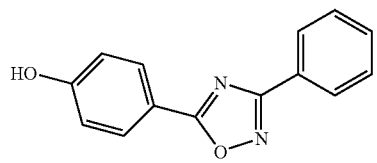 [SMILES: Oc1ccc(-c2nc(-c3ccccc3)no2)cc1]

(Z)-N'-hydroxy-4-methoxybenzamidine (compound 24-structure shown below): A solution of anisonitrile (300 mg, 2.25 mmol) and hydroxylamine (275 μL, 9.01 mmol) in ethanol (5.0 mL) was refluxed for 3 hours. The reaction was cooled and then concentrated in vacuo to give the product (370 mg, 99%), which immediately formed white crystals and was taken to the next step without further purification. A small quantity was purified by column chromatography over silica gel (Hex/EtOAc 1:8) to give the product (370 mg, 99%) as a white solid. $^1$H NMR (500 MHz, CDCL$_3$) δ(ppm): 3.83 (3H, s), 4.86 (2H, bs), 6.91 (2H, d, J=8.4 Hz), 7.56 (2H, d, J=8.4 Hz). $^{13}$C NMR (125 MHz, CDCL$_3$) δ(ppm): 55.5 (CH3), 114.2 (CH), 125.1, 127.4 (CH), 152.7, 161.2. MS (FAB$^+$): 167 (MH$^+$). HRMS for O$_8$H$_{10}$N$_2$O$_2$ (MH$^+$): calculated: 167.0821; found 167.0803.

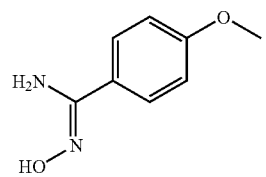

4-fluorobenzoyl-O-4-methoxybenzamidoxime (compound 25-structure shown below): (Z)-N'-hydroxy-4-methoxybenzamidine (200 mg, 1.20 mmol) was added to methylene chloride (14.0 mL) and N-ethyldiisopropylamine (420 μL, 2.41 mmol). The solution was cooled to 0° C. and placed under nitrogen. Then 4-Fluorobenzoyl chloride (215 μL, 1.81 mmol) was added dropwise and the mixture was stirred for 1 hour at 0° C. The solution was allowed to warm to room temperature and was then stirred for 21 hours. Ethyl acetate (20 mL) was poured into the mixture and the solution was washed with water (20 mL) and then brine (20 mL). The organic layer was then dried with MgSO$_4$ and concentrated in vacuo. The solid residue was purified using column chromatography over silica gel (EtOAc/Hex 1:8 to 3:1) to give the product as a white powder (340 mg, 98%). $^1$H NMR (500 MHz, CDCL$_3$) δ(ppm): 3.84 (3H, bs), 5.16 (2H, bs), 6.93 (2H, d, J=8.8 Hz), 7.14 (2H, t, J=8.7 Hz), 7.70 (2H, d, J=8.8 Hz), 8.10 (2H, dd, J=8.7, 9.4 Hz). $^{13}$C NMR (75 MHz, CDCL$_3$) δ(ppm): 55.6(CH$_3$), 114.3 (CH), 115.9 (2 CH, d, J=21.6 Hz), 123.4, 126.1, 128.5 (CH), 132.2 (2 CH, d, J=9.4 Hz), 157.3, 162.1, 163.4, 165.9 (1C, d, J=254.3 Hz). $^{19}$F (282 MHz, CDCL$_3$) δ(ppm): $^-$105.3-$^-$105.4 (1F, m). MS (FAB$^+$): 289 (MH$^+$). HRMS for C$_{15}$H$_{13}$FN$_2$O$_3$ (MH$^+$): calculated: 289.0988; found 289.0999.

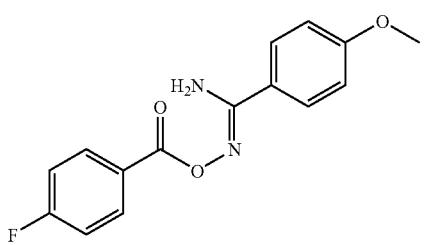 [SMILES: COc1ccc(/C(N)=N/OC(=O)c2ccc(F)cc2)cc1]

5-(4-fluorophenyl)-3-(4-methoxyphenyl)-1,2,4-oxadiazole (compound 26-structure shown below): 4-Fluorobenzoyl-O-4-methoxybenzamidoxime (300 mg, 1.04 mmol) was placed under nitrogen and THF (15.0 mL) was added. Then tetrabutylammonium fluoride (1.0 M in THF, 1.04 mmol, 1.0 mL) was added dropwise the solution was stirred at room temperature for 17 hours 45 minutes. The solvent was removed under reduced pressure and the product was purified by column chromatography over silica gel (EtOAc/Hex 1:2 to 1:1) and crystallized from hot hexane to give a white crystalline material (169 mg, 60%). $^1$H NMR (300 MHz, CDCL$_3$) δ(ppm): 3.82 (3H, s), 6.95 (2H, d, J=8.8 Hz), 7.17 (2H, t, J=8.6 Hz), 8.03 (2H, d, J=8.6 Hz), 8.10 (2H, dd, J=8.8, 9.4 Hz). $^{13}$C NMR (75 MHz, CDCL$_3$) δ(ppm): 55.6(CH$_3$), 114.5 (CH), 116.6 (2CH, d, J=21.7 Hz), 119.5, 121.0 (C, d, J=1.5 Hz), 129.3, 130.8 (2CH, d, J=9.0 Hz), 162.2, 163.9, 167.3, 168.9. MS (FAB$^+$): 271 (MH$^+$). HRMS for C$_{15}$H$_{11}$FN$_2$O$_2$ (MH$^+$): calculated: 271.0883; found 271.0888.

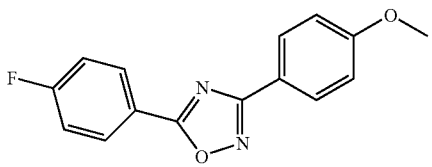 [SMILES: COc1ccc(-c2noc(-c3ccc(F)cc3)n2)cc1]

5-(4-(benzyloxy)phenyl)-3-(4-methoxyphenyl)-1,2,4-oxadiazole (compound 27-structure shown below): EDC (246 mg, 1.27 mmol) in methylene chloride (5.0 mL) was added to a solution of 4-benzyloxybenzoic acid (279 mg, 1.21 mmol) and benzylhydroxyamidine (201 mg, 1.21 mmol) in methylene chloride (10.0 mL). The mixture was stirred for 6 hours and checked by TLC for completion. Then tetrabutylammonium fluoride (1.0 M in THF, 2.42 mmol 2.3 mL) was added dropwise and the solution was stirred at room temperature for 13 hours 30 minutes. The solid residue was purified by column chromatography over silica gel (EtOAc/Hex 1:4 to 1:2) and was crystallized from ethyl acetate to give a white crystalline material (74 mg 17%). $^1$H NMR (500 MHz, CDCL$_3$) δ(ppm): 3.88 (3H, s), 5.15 (2H, s), 7.01 (2H, d, J=8.8 Hz), 7.10 (2H, d, J=8.8 Hz), 7.40-7.46 (4H, m), 8.10 (2H, d, J=8.6 Hz), 8.15 (2H, d, J=8.6 Hz). $^{13}$C NMR (125 MHz, CDCL$_3$) δ(ppm): 55.6 (CH$_3$), 70.4 (CH$_2$), 114.4 (CH), 115.5 (CH), 117.4, 119.8, 127.8 (CH), 128.5 (CH), 128.9 (CH), 129.3 (CH), 130.3 (CH), 136.3, 162.0, 162.4, 168.7, 175.5. MS (FAB$^+$): 359 (MH$^+$). HRMS for C$_{22}$H$_{18}$N$_2$O$_3$ (MH$^+$): calculated: 359.1396; found 359.1392.

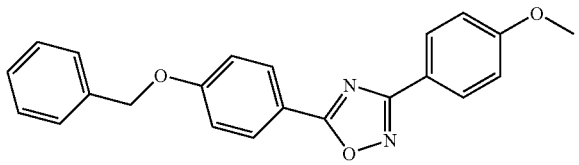 [SMILES: COc1ccc(-c2noc(-c3ccc(OCc4ccccc4)cc3)n2)cc1]

4-(3-(4-methoxyphenyl)-1,2,4-oxadiazol-5-yl)phenol (compound 28-structure shown below): 5-(4-(Benzyloxy)phenyl)-3-(4-methoxyphenyl)-1,2,4-oxadiazole (50 mg, 139 μmol) and 10% Pd/C (1 mg, 10 μmol) were suspended in methanol (3.0 mL) and THF (3.0 mL). The solution was stirred in a round bottom flask fitted with a condenser and septa and placed under H$_2$ at 55° C. for 95 hours. The solution was filtered through Celite and the solvent was removed under reduced pressure and then purified by silica gel column chromatography (EtOAc/Hex 1:2) to give the product (3 mg, 9%) as a white solid. $^1$H NMR (500 MHz, CDCL$_3$) δ(ppm): 3.88 (3H, s), 5.55 (1H, s), 6.98 (2H, d, J=9.0 Hz), 7.01 (2H, d, J=8.4 Hz), 8.01 (2H, d, J=9.0 Hz), 8.12 (2H, d, J=8.2 Hz). $^{13}$C NMR (125 MHz, CDCL$_3$) δ(ppm): 55.6 (CH$_3$), 114.4 (CH), 116.3 (CH), 117.4, 119.7, 129.3 (CH), 130.6 (CH), 159.6, 162.1, 168.7, 175.4. MS (FAB$^+$): 269 (MH$^+$). HRMS for C$_{15}$H$_{12}$N$_2$O$_3$ (MH$^+$): calculated: 269.0926; found 269.0929.

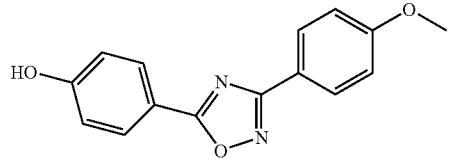 [SMILES: COc1ccc(-c2noc(-c3ccc(O)cc3)n2)cc1]

(Z)-4-(phenoxy)-O-(4-fluorobenzoyl)benzamidoxime (compound 29-structure shown below): (Z)-N'-hydroxy-4-phenoxybenzamidine (140 mg, 0.61 mmol) was placed under nitrogen and dissolved in methylene chloride (3.0 mL) and N-ethyldiisopropylamine (220 μL, 1.23 mmol) was added. The solution was cooled to 0° C. and then 4-Fluorobenzoyl chloride was added dropwise and the mixture was stirred for hour at 0° C. The solution was allowed to warm to room temperature and was then stirred for 18 hours. Ethyl acetate (25 mL) was poured into the mixture and the solution was washed with water (25 mL) and then brine (25 mL). The organic layer was then dried with MgSO$_4$ and concentrated in vacuo. The crude solid was purified using silica gel column chromatography (EtOAc/Hex 1:8 to 1:6) and recrystallized from hot hexane to give the product as clear crystals. $^1$H NMR (500 MHz, CDCL$_3$) δ(ppm): 5.20 (2H, bs), 7.05 (2H, t, J=6.8), 7.16-7.20 (2H, m), 7.40 (2H, t, J=7.6 Hz), 7.74 (2H, d, J=8.2 Hz), 8.12 (2H, d, J=5.8 Hz). $^{13}$C NMR (125 MHz, CDCL$_3$) δ(ppm): 115.9 (CH, d, J=22.2 Hz), 118.5 (CH), 119.8 (CH), 124.3 (CH), 125.6, 126.0 (C, d, J=3.5 Hz), 128.8 (CH), 130.2 (CH), 132.2 (CH, d, J=9.1 Hz), 156.3, 157.0, 160.3, 163.3, 165.9 (C, d, J=253.1 Hz), 174.9. $^{19}$F (282 MHz, CDCL$_3$) δ(ppm): $^-$105.1-$^-$105.2 (1F, m). MS (FAB$^+$): 351 (MH$^+$). HRMS for C$_{20}$H$_{15}$FN$_2$O$_3$ (MH$^+$): calculated: 351.1145; found 351.1137.

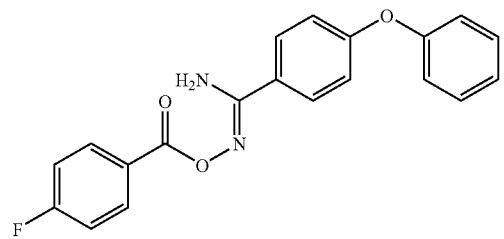 [SMILES: N/C(=N\OC(=O)c1ccc(F)cc1)c1ccc(Oc2ccccc2)cc1]

5-(4-fluorophenyl)-3-(4-phenoxyphenyl)-1,2,4-oxadiazole (compound 30-structure shown below): (Z)-4-Phenoxy-O-4-fluorobenzamidoxime (32 mg, 91 mmol) was placed under nitrogen and THF (3.0 mL) was added. Then tetrabutylammonium fluoride (1.0 M in THF, 26 μL) was added dropwise the solution was stirred at room temperature for 21 hours. The solvent was removed under reduced pressure and the solid residue was purified by silica gel column chromatography (EtOAc/Hex 1:2) to give the product (30 mg, 99%) as a white solid. $^1$H NMR (500 MHz, CDCL$_3$) δ(ppm): 7.08-7.11 (4H, m), 7.16-7.19 (1H, m), 7.22-7.25 (2H, m), 7.39 (2H, dd, J=8.6, 7.6 Hz), 8.12 (2H, d, J=8.8 Hz), 8.22 (2H, dd, J=9.0, 5.2 Hz). $^{13}$C NMR (125 MHz, CDCL$_3$) δ(ppm): 116.6 (CH, d, J=22.5 Hz), 116.6 (CH), 120.0 (CH), 120.9 (C, d, J=2.5 Hz), 121.6, 124.4, 129.5 (CH), 130.2 (CH), 130.8 (CH, d, J=2.5 Hz), 156.3, 160.4, 164.6, 167.7 (C, d, J=256.3 Hz), 174.9. $^{19}$F (282 MHz, CDCL$_3$) δ(ppm): $^-$105.1-$^-$105.2 (1F, m). MS (FAB⁺): 333 (MH⁺). HRMS for $C_{20}H_{13}FN_2O_2$ (MH⁺): calculated: 332.0961; found 332.0946.

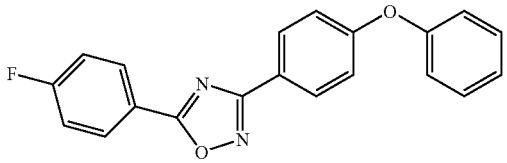 [SMILES: Fc1ccc(-c2nc(-c3ccc(Oc4ccccc4)cc3)no2)cc1]

(4-methoxyphenoxy)(tert-butyl)dimethylsilane (compound 31-structure shown below): Imidazole (1.80 g, 26.1 mmol) and p-methoxyphenol (1.62 g, 13.05 mmol) were suspended in THF (30 mL) and placed under nitrogen. Tert-butyldimethylsilyl chloride (2.23 g, 14.36 mmol) was added and the mixture was stirred for 15 hours at room temperature. The thick white mixture was diluted with water (50 mL) and extracted with ether (3×15 mL). The organic solvent was removed under reduced pressure to give the product as a clear liquid (2.33 g, 75%). Characterization matched literature.

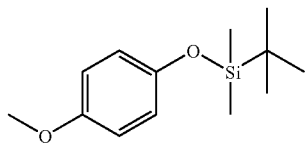 [SMILES: COc1ccc(O[Si](C)(C)C(C)(C)C)cc1]

4-(4-methoxyphenoxy)benzonitrile (compound 32-structure shown below): To a stirred solution of proazaphosphatrane (15 mg, 41 mmol) in DMF (20.0 mL) was added the aryl fluoride (50 mg, 41 mmol) under nitrogen. After two minutes of stirring, the silated ether (108 mg, 45 mmol) was added. The reaction mixture was heated at 80 C for 21 hours and then cooled to room temperature. A saturated brine solution (5.0 mL) was added and the product was extracted with EtOAc (3×10 mL) and the organic layer was dried with sodium sulfate. The solvent was removed using reduced pressure and the crude material was purified using column chromatography Hex/EtOAc (8:1) to give the pure product as a white solid (36 mg, 39%). Characterization matched literature.

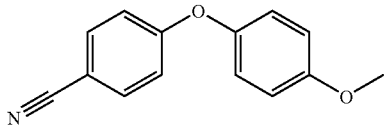 [SMILES: COc1ccc(Oc2ccc(C#N)cc2)cc1]

(Z)-4-(4-methoxyphenoxy)-N'-hydroxybenzamidine (compound 33-structure shown below): 4-(4-Methoxyphenoxy)benzonitrile (581 mg, 2.58 mmol) was dissolved in ethanol (10.0 mL) and hydroxylamine (630 µL, 10.32 mmol) was added. The mixture was refluxed for 1 hour and the reaction was cooled and then concentrated in vacuo to give the crude product which was taken to the next step without further purification (636 mg, 95%). ¹H NMR (500 MHz, CDCL₃) δ(ppm): 3.81 (1H, s), 4.87 (1H, bs), 6.88-6.94 (4H, m), 6.99 (2H, d, J=9.2 Hz), 7.55 (2H, d, J=9.0 Hz). ¹³C NMR (125 MHz, CDCL₃) δ(ppm): 55.8 (CH₃), 115.2 (CH), 117.4 (CH), 121.4 (CH), 126.6 (CH), 127.6, 149.5, 152.5, 156.5, 160.4. MS (FAB⁺): 259 (MH⁺). HRMS for $C_{14}H_{14}N_2O_3$ (MH⁺): calculated: 259.1083; found 259.1100.

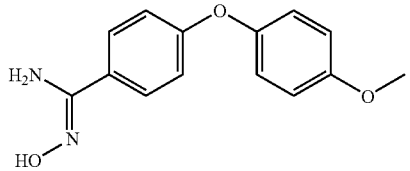 [SMILES: COc1ccc(Oc2ccc(/C(N)=N/O)cc2)cc1]

4-(4-methoxybenzyloxy)phenyl-O-4-fluorobenzoylbenzamidoxime (compound 34-structure shown below): (Z)-4-(4-Methoxyphenoxy)-N'-hydroxy-benzamidine (300 mg, 1.16 mmol) was added to methylene chloride (6.0 mL) and N-ethyldiisopropylamine (304 mg, 2.33 mmol). The solution was cooled to 0° C. and placed under nitrogen. 4-Fluorobenzoyl chloride (282 mg, 1.74 mmol) was then added dropwise and the mixture was stirred for 1 hour at 0° C. The solution was allowed to warm to room temperature and was then stirred for 20 hours. Ethyl acetate (25 mL) was poured into the mixture and the solution was washed with water (25 mL) and then brine (25 mL). The organic layer was then dried with MgSO₄ and concentrated in vacuo. The solid material was purified using silica gel column chromatography (EtOAc/Hex 1:8 to 3:1) to give the product as white crystals (320 mg, 72%). ¹H NMR (500 MHz, CDCL₃) δ(ppm): 3.82 (2H, s), 5.12 (2H, bs), 6.91 (2H, d, J=9.2 Hz), 6.97 (2H, d, J=9.0 Hz), 7.00 (2H, d, J=9.2 Hz), 7.15 (2H, t, J=8.7 Hz), 7.70 (2H, d, J=9.0 Hz), 8.11 (2H, m). ¹³C NMR (125 MHz, CDCL₃) δ(ppm): 55.7 (CH₃), 115.0, 115.7 (CH, d, J=22.5 Hz), 117.3 (CH), 121.3 (CH), 124.8, 125.9, 128.5, 132.0 (CH, d, J=9.4 Hz), 149.0, 156.4, 156.9, 162.2 (C, d, J=237.7 Hz), 164.8, 166.8. ¹⁹F (282 MHz, CDCL₃) δ(ppm): ⁻105.2-⁻105.4 (1F, m). MS (FAB⁺): 380 (MH⁺). HRMS for $C_{21}H_{17}FN_2O_4$ (MH⁺): calculated: 380.1172; found 380.1151.

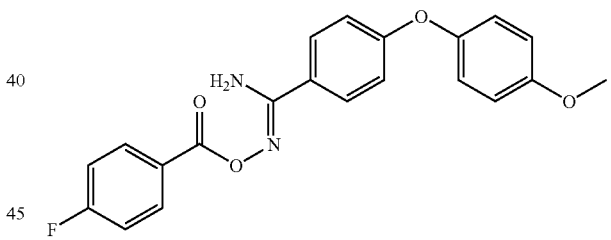

3-(4-(4-methoxyphenoxy)phenyl)-5-(4-fluorophenyl)-1,2,4-oxadiazole (compound 35-structure shown below): 4-(4-Methoxybenzyloxy)phenyl-O-4-fluorobenzoylbenzamidoxime (293 mg, 0.77 mmol) was placed under nitrogen and THF (10.0 mL) was added. Then tetrabutylammonium fluoride (0.77 µL, 0.77 mmol) was added dropwise and the solution was stirred at room temperature for 13 hours 30 minutes. The crude solid was purified by silica gel column chromatography (EtOAc/Hex 1:2 to 1:1) and was crystallized from hot hexane to give a white crystalline material (259 mg, 93%). ¹H NMR (500 MHz, CDCL₃) δ(ppm): 3.79 (2H, s), 6.90 (2H, d, J=9.0 Hz), 7.01 (4H, t, J=9.2 Hz), 7.18 (2H, t, J=8.7 Hz), 8.06 (2H, d, J=8.8 Hz), 8.16 (2H, dd, J=8.9, 5.3 Hz). ¹³C NMR (125 MHz, CDCL₃) δ(ppm): 55.7 (CH₃), 115.1 (CH), 116.5 (CH, d, J=22.5 Hz), 117.3 (CH), 120.8, 121.6 (CH), 129.3, 130.6 (CH, d, J=8.8 Hz), 149.0, 156.5, 161.4, 165.5 (C, d, J=252.9 Hz), 168.6, 174.6. ¹⁹F (282 MHz, CDCL₃) δ(ppm): ⁻105.1-⁻105.2 (1F, m). MS (FAB⁺): 362 (MH⁺). HRMS for $C_{21}H_{15}FN_2O_3$ (MH⁺): calculated: 362.1067; found 362.1063.

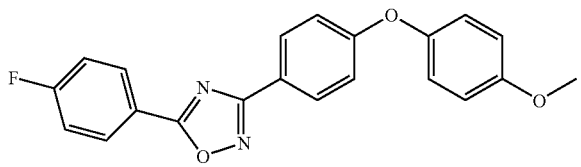 [SMILES: COc1ccc(Oc2ccc(-c3noc(-c4ccc(F)cc4)n3)cc2)cc1]

4-(4-(5-(4-fluorophenyl)-1,2,4-oxadiazol-3-yl)phenoxy) phenol (compound 36-structure shown below): 3-(4-(4-Methoxyphenoxy)phenyl)-5-(4-fluorophenyl)-1,2,4-oxadiazole (150 mg, 0.414 mmol) was suspended in dry methylene chloride (10.0 mL) and the mixture was placed under nitrogen and cooled to −80 C. Boron tribromide (1.0 M in CH2Cl2, 2.07 mmol) was added dropwise over 10 minutes. The mixture was allowed to warm to room temperature and stirred for 19 hours 30 minutes. The reaction mixture was then cooled to −80 C and H2O (2.0 mL) was added dropwise. The organic layer was removed under reduced pressure and the compound was purified by column chromatography (Hex/EtOAc 2:1) to give a white powder (144 mg, 100%). $^1$H NMR (500 MHz, DMSO-d$_6$) δ(ppm): 6.83 (2H, d, J=8.8 Hz), 6.98 (2H, d, J=8.8 Hz), 7.04 (2H, t, J=8.8 Hz), 7.49 (2H, t, J=8.8 Hz), 8.03 (2H, d, J=9.0 Hz), 8.23 (2H, dd, J=8.8, 5.4 Hz), 9.49 (1H, s). $^{13}$C NMR (125 MHz, DMSO-d$_6$) δ(ppm): 116.5 (CH), 116.9 (CH, d, J=22.5 Hz), 116.9 (CH), 119.7, 121.6 (CH, d, J=3.8 Hz), 121.7 (CH), 129.1, 130.8 (CH, d, J=10.0 Hz), 146.6, 154.5, 161.3, 164.9 (C, d, J=251.2 Hz), 167.8, 174.4. $^{19}$F (282 MHz, DMSO-d$_6$) δ(ppm): ⁻105.1-⁻105.2 (1F, m). MS (FAB⁺): 348 (MH⁺). HRMS for $C_{20}H_{13}FN_2O_3$ (MH⁺): calculated: 348.0910; found 348.0897.

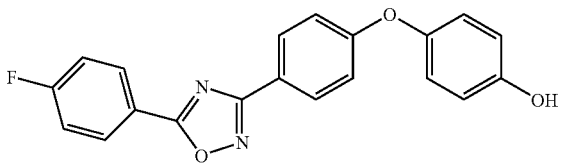 [SMILES: Oc1ccc(Oc2ccc(-c3noc(-c4ccc(F)cc4)n3)cc2)cc1]

4-(4-(5-(4-fluorophenyl)-1,2,4-oxadiazol-3-yl)phenoxy) phenyl dihydrogen phosphate (compound 37-structure shown below): A solution of 4-(4-(5-(4-fluorophenyl)-1,2,4-oxadiazol-3-yl)phenoxy)phenol (20 mg, 58 μmol) in dry pyridine (4.0 mL) was slowly added with stirring to phosphorus oxychloride (9 mg, 58 μmol). The mixture was refluxed for 40 minutes and then allowed to cool to room temperature and then was slowly added to ice. Once cooled, the water was removed under reduced pressure and the solid material was purified by silica gel column chromatography (CH$_2$Cl$_2$/MeOH 95:5) to give the product as an off white solid (3 mg, 12%). $^1$H NMR (300 MHz, DMSO-d$_6$) δ(ppm): 7.02-7.11 (4H, m), 7.22 (2H, d, J=7.2 Hz), 7.50 (2H, td, J=9.0, 2.6 Hz), 8.04 (2H, dd, J=8.8, 2.4 Hz), 8.21-8.26 (2H, m). $^{19}$F (282 MHz, DMSO-d$_6$) δ(ppm): ⁻105.3-⁻105.4 (1F, m). $^{31}$P NMR (121 MHz, DMSO-d$_6$) δ(ppm): −67.08 (1P, s).

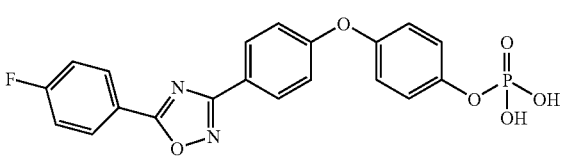 [SMILES: O=P(O)(O)Oc1ccc(Oc2ccc(-c3noc(-c4ccc(F)cc4)n3)cc2)cc1]

4-(pyrazin-2-yloxy)benzonitrile (compound 38-structure shown below): 2-Iodopyrazine (2.00 g, 9.42 mmol), copper(I) iodide (366 mg, 1.88 mmol), cesium carbonate (6.14 g, 18.84 mmol), 4-hydroxybenzonitrile (1.68 g, 14.13 mmol) and N,N-dimethylglycine hydrochloride (398 mg, 2.83 mmol) were dried and placed under nitrogen and then degassed 1,4-dioxane (25.0 mL) was added. The whole mixture was heated at 90° C. for 138 hours. The cooled mixture was partitioned between ethyl acetate (50 mL) and water (50 mL). The organic layer was separated and the aqueous layer was extracted with ethyl acetate (2×50 mL). The organic layers were combined and washed with brine (50 mL) and dried with Na$_2$SO$_4$ and concentrated in vacuo. The crude solid was placed on a silica gel column and purified (EtOAc/Hex 1:8) to give the product as an off white solid (1.61 g, 87%). $^1$H NMR (300 MHz, CDCL$_3$) δ(ppm): 7.31 (2H, d, J=9.1 Hz), 7.74 (2H, d, J=9.1 Hz), 8.14 (1H, dd, J=2.4, 1.4 Hz), 8.37 (1H, d, J=2.4 Hz), 8.51 (1H, s). $^{13}$C NMR (75 MHz, CDCL$_3$) δ(ppm): 109.0, 118.5, 122.0 (CH), 134.1 (CH), 136.4 (CH), 139.8 (CH), 141.1 (CH), 156.7, 159.1. MS (FAB⁺): 198 (MH⁺). HRMS for $C_{11}H_7N_3O$ (MH⁺): calculated: 198.0667; found 198.0661.

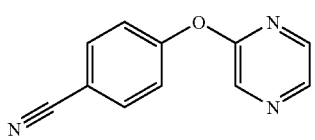

(Z)-N'-hydroxy-4-(pyrazin-2-yloxy)benzamidine (compound 39-structure shown below): 4-(Pyrazin-2-yloxy)benzonitrile (1.00 g, 5.06 mmol) was dissolved in ethanol (15.0 mL) hydroxylamine (625 μL, 20.28 mmol) was added and the mixture was refluxed for 17 hours. The reaction was cooled and then concentrated in vacuo to give the crude product, which immediately formed white crystals and was taken to the next step without further purification (1.16 g, 100%). A small quantity was purified by column chromatography (Hex/EtOAc 1:8) to give the pure product. $^1$H NMR (500 MHz, DMSO-d$_6$) δ(ppm): 5.85 (2H, s), 7.21 (2H, d, J=8.4 Hz), 7.73 (2H, d, J=8.6 Hz), 8.21 (1H, dd, J=2.7, 1.5 Hz), 8.39 (1H, d, J=2.8 Hz), 8.57 (1H, d, J=1.4 Hz), 9.66 (1H, s). $^{13}$C NMR (75 MHz, DMSO-d$_6$) δ(ppm): 120.9 (CH), 126.9 (CH), 130.4, 135.7 (CH), 139.1 (CH), 141.2 (CH), 150.3, 153.4, 159.5. MS (FAB⁺): 231 (MH⁺). HRMS for $C_{11}H_{10}N_4O_2$ (MH⁺): calculated: 231.0882; found 231.0892.

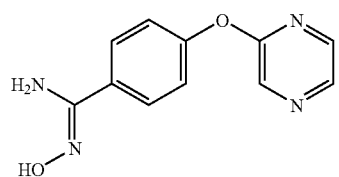 [SMILES: N/C(=N\O)c1ccc(Oc2cnccn2)cc1]

2-(4-(5-(4-(benzyloxy)phenyl)-1,2,4-oxadiazol-3-yl)phenoxy)pyrazine (compound 40-structure shown below): (Z)-N'-hydroxy-4-(pyrazin-2-yloxy)benzamidine (22 mg, 97 μmol) and acid chloride (3 mg, 126 μmol) were suspended in pyridine (5.0 mL) the solution was refluxed for 19 hours. The reaction mixture was then cooled to room temperature and solvent was removed under reduced pressure and the residue solid was purified by silica gel column chromatography (Hex/EtOAc 1:2) to give the product as a white solid (26 mg, 64%). $^1$H NMR (500 MHz, CDCL$_3$) δ(ppm): 5.14 (2H, s), 7.02 (2H, d, J=9.0 Hz), 7.12 (1H, d, J=8.8 Hz), 7.31 (1H, d, J=8.8 Hz), 7.34-7.38 (1H, m), 7.39-7.46 (5H, m), 8.07 (2H, d, J=8.8 Hz), 8.16 (1H, d, J=9.0 Hz), 8.24 (1H, d, J=8.8 Hz). $^{13}$C NMR (125 MHz, CDCL$_3$) δ(ppm): 70.4 (CH$_2$), 114.8 (CH), 115.6 (CH), 121.7 (CH), 127.7 (CH), 128.5 (CH), 128.5 (CH), 128.9 (CH), 129.0 (CH), 129.5 (CH), 130.3 (CH), 132.6 (CH), 136.3, 139.2, 141.4, 163.4. MS (FAB$^+$): 423 (MH$^+$). HRMS for C$_{25}$H$_{18}$N$_4$O$_3$ (MH$^+$): calculated: 423.1457; found 423.1448.

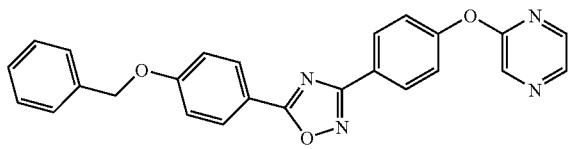 [SMILES: c1ccc(COc2ccc(-c3nc(-c4ccc(Oc5cnccn5)cc4)no3)cc2)cc1]

4-(pyridin-2-yloxy)benzonitrile (compound 41-structure shown below): 4-Hydroxybenzonitrile (1.00 g, 8.39 mmol) was dissolved in anhydrous DMSO (5.0 mL) and was slowly added a solution of potassium tert-butoxide in THF (1.0 M, 16.8 mmol). The solution was stirred for 2 hours 30 minutes. A solution of 2-bromopyridine (2.65 g, 16.8 mmol) in DMSO (5.0 mL) was then added to the reaction mixture the whole was heated at 160° C. for 115 hours. The cooled mixture was partitioned between ethyl acetate (100 mL) and water (100 mL). The organic layer was separated and the aqueous layer was extracted with ethyl acetate (2×100 mL). The organic layers were dried with MgSO$_4$, filtered and concentrated in vacuo. The crude solid was placed on a silica gel column and purified (EtOAc/Hex 1:6) to give the product as a light yellow solid (1.04 g, 63%). $^1$H NMR (500 MHz, CDCL$_3$) δ(ppm): 7.01 (1H, d, J=8.2 Hz), 7.10 (1H, dd, J=7.2, 5.0 Hz), 7.24 (2H, d, J=9.0 Hz), 7.68 (2H, d, J=8.8 Hz), 7.77 (1H, ddd, J=8.3, 7.3, 2.0 Hz), 8.22 (1H, dd, J=5.0, 2.0 Hz). $^{13}$C NMR (125 MHz, CDCL$_3$) δ(ppm): 108.0, 112.8 (CH), 118.9, 120.0 (CH), 121.6 (CH), 134.1 (CH), 140.2 (CH), 147.9 (CH), 158.2, 162.5. MS (FAB$^+$): 197 (MH$^+$). HRMS for C$_{12}$H$_8$N$_2$O (MH$^+$): calculated: 197.0713; found 197.0715.

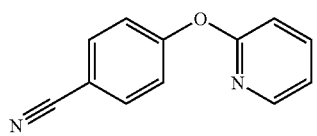 [SMILES: N#Cc1ccc(Oc2ccccn2)cc1]

(Z)-N'-hydroxy-4-(pyridin-2-yloxy)benzamidine (compound 42-structure shown below): 4-(Pyridin-2-yloxy)benzonitrile (701 mg, 3.57 mmol) was dissolved in ethanol (14.0 mL), and hydroxylamine (472 mg, 14.3 mmol) was added and the mixture was refluxed for 16 hours. The reaction was cooled to room temperature and then concentrated in vacuo to give the product as a yellow syrup and was taken to the next step without further purification (818 mg, 100%). $^1$H NMR (500 MHz, CDCL$_3$) δ(ppm): 4.91 (2H, bs), 6.94 (1H, dt, J=8.4, 0.8 Hz), 7.02 (1H, ddd, J=7.2, 5.0, 0.8 Hz), 7.16 (2H, d, J=8.6 Hz), 7.66 (2H, d, J=8.6 Hz), 7.71 (1H, ddd, J=8.2, 7.2, 2.0 Hz), 8.21 (1H, ddd, J=5.0, 2.0, 0.8 Hz). $^{13}$C NMR (125 MHz, CDCL$_3$) δ(ppm): 112.1 (CH), 119.1 (CH), 121.4 (CH), 127.6 (CH), 129.0 (CH), 139.8 (CH), 147.9 (CH), 152.4, 155.8, 163.4. MS (FAB$^+$): 230 (MH$^+$). HRMS for C$_{12}$H$_{11}$N$_3$O$_2$ (MH$^+$): calculated: 230.0930; found 230.0934.

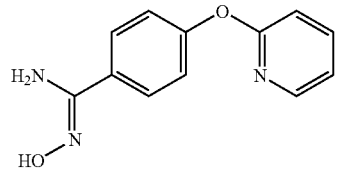 [SMILES: N/C(=N\O)c1ccc(Oc2ccccn2)cc1]

2-(4-(5-(4-(benzyloxy)phenyl)-1,2,4-oxadiazol-3-yl)phenoxy)pyridine (compound 43-structure shown below): (Z)-N'-Hydroxy-4-(pyridin-2-yloxy)benzamidine (339 mg, 137 μmol) and 4-benzyloxybenzoyl chloride (24 mg, 106 μmol) were suspended in pyridine (2.0 mL) the solution was refluxed for 21 hours. The reaction mixture was then cooled to room temperature and solvent was removed under reduced pressure and the residue was purified by silica gel column chromatography (Hex/EtOAc 2:1) to give the product as a white solid (20 mg, 46%). $^1$H NMR (500 MHz, CDCL$_3$) δ(ppm): 5.16 (2H, s), 6.99 (1H, d, J=8.2 Hz), 7.05 (1H, ddd, J=7.2, 5.0, 0.80 Hz), 7.11 (2H, d, J=8.8 Hz), 7.27 (2H, d, J=8.8 Hz), 7.34-7.38 (1H, m), 7.40-7.46 (4H, m), 7.73 (1H, ddd, J=8.8, 8.2, 2.0 Hz), 8.16 (2H, d, J=9.0 Hz), 8.20 (2H, d, J=8.6 Hz), 8.24 (1H, dd, J=5.0, 2.0Hz). $^{13}$C NMR (125 MHz, CDCL$_3$) δ(ppm): 70.4 (CH$_2$), 112.3 (CH), 115.5 (CH), 117.3, 119.3 (CH), 121.4 (CH), 123.5, 127.7 (CH), 128.5 (CH), 128.9 (CH), 129.3 (CH), 130.3 (CH), 136.2, 139.9 (CH), 148.0 (CH), 156.8, 162.5, 163.3, 168.5, 175.7. MS (FAB$^+$): 422 (MH$^+$). HRMS for C$_{26}$H$_{19}$N$_3$O$_3$ (MH$^+$): calculated: 422.1505; found 422.1505.

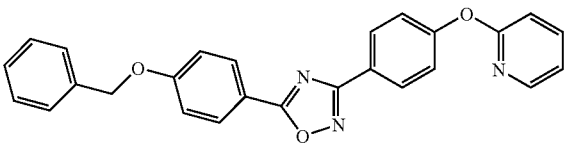 [SMILES: c1ccc(COc2ccc(-c3nc(-c4ccc(Oc5ccccn5)cc4)no3)cc2)cc1]

4-(3-(4-(pyridin-2-yloxy)phenyl)-1,2,4-oxadiazol-5-yl)phenol (compound 44-structure shown below): 2-(4-(5-(4-(Benzyloxy)phenyl)-1,2,4-oxadiazol-3-yl)phenoxy)pyridine (310 mg, 376 μmol) was placed in a single neck round bottom flask, suspended in methanol (5.0 mL) and THF (5.0 mL) and 10% Pd/C (0.5 mg, 5.0 μmol) was added. A condenser was placed on top of the flask and then sealed. The solution was stirred under H$_2$ at 55° C. for 22 hours. While hot, the solution was filtered through Celite washed with additional methanol and the solvent was removed under reduced pressure. The solid residue was purified by silica gel column chromatography (EtOAc/Hex 1:2) to give the product as a white solid (7 mg, 3%). $^1$H NMR (500 MHz, CDCL$_3$) δ(ppm): 7.00 (2H, d, J=8.8 Hz), 7.14 (1H, d, J=8.2 Hz), 7.05 (1H, ddd, J=7.3, 5.0, 1.0 Hz), 7.32 (2H, d, J=8.8 Hz), 7.92 (1H, ddd, J=8.8, 8.2, 2.0 Hz), 8.03 (2H, d, J=8.8 Hz), 8.11 (2H, d, J=8.8 Hz), 8.21 (1H, ddd, J=5.0, 2.0, 1.0 Hz). $^{13}$C NMR (125 MHz, CDCL$_3$) δ(ppm): 112.2 (CH), 114.1 (CH), 116.3 (CH), 119.7 (CH), 121.5 (CH), 122.4, 128.7 (CH), 130.1 (CH), 140.5 (CH), 147.6 (CH), 156.6, 162.1, 162.4 167.6, 175.5. MS (FAB$^+$): 332 (MH$^+$). HRMS for C$_{19}$H$_{13}$N$_3$O$_3$ (MH$^+$): calculated: 332.1035; found 332.1049.

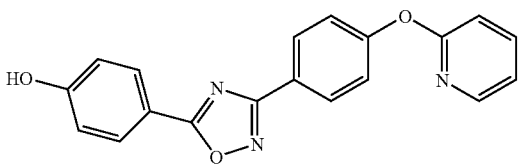 [SMILES: Oc1ccc(-c2nc(-c3ccc(Oc4ccccn4)cc3)no2)cc1]

4-(pyridin-3-yloxy)benzonitrile (compound 45-structure shown below): A solution of potassium tert-butoxide in THF (1.0 M, 8.73 mmol) was slowly added to a solution of 3-hydroxypyridine (830 mg, 8.73 mmol) in anhydrous DMF (5.0 mL) and was stirred for 2 hours. A solution of 4-iodobenzonitrile in DMF (5.0 mL) was then added to the reaction mixture and was then heated at 160° C. for 18 hours. The mixture was cooled and partitioned between ethyl acetate (50 mL) and water (50 mL). The organic layer was separated and the aqueous layer was extracted with ethyl acetate (2×50 mL). The organic layers were dried with MgSO$_4$, filtered and concentrated in vacuo. The crude oil was placed on a silica gel column and purified (EtOAc/Hex 1:8) to give the product as a yellow oil (640 mg, 75%). $^1$H NMR (500 MHz, CDCL$_3$) δ(ppm): 7.05 (2H, d, J=9.0 Hz), 7.10 (1H, dd, J=8.4, 4.6 Hz), 7.24 (1H, ddd, J=8.4, 2.6, 1.6 Hz), 7.65 (2H, d, J=9.0 Hz), 8.46 (1H, d, J=2.6 Hz), 8.22 (1H, dd, J=4.6, 1.6 Hz). $^{13}$C NMR (125 MHz, CDCL$_3$) δ(ppm): 107.1, 118.3 (CH), 118.6, 124.7 (CH), 127.5 (CH), 134.5 (CH), 142.8 (CH), 146.4 (CH), 151.8, 160.9. MS (FAB$^+$): 197 (MH$^+$). HRMS for $C_{12}H_8N_2O$ (MH$^+$): calculated: 197.0713; found 197.0696.

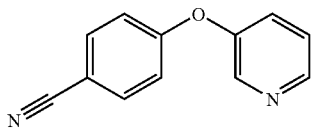 [SMILES: N#Cc1ccc(Oc2cccnc2)cc1]

(Z)-N'-hydroxy-4-(pyridin-3-yloxy)benzamidine (compound 46-structure shown below): 4-(Pyridin-3-yloxy)benzonitrile (486 mg, 2.48 mmol) was dissolved in ethanol (10.0 mL) then hydroxylamine (1.0 mL, 9.9 mmol) was added and the mixture was refluxed for 4 hours. The reaction was cooled to room temperature and concentrated in vacuo to give the product which immediately formed yellow solid (565 mg, 100%) which was taken to the next step without further purification. $^1$H NMR (500 MHz, DMSO-d$_6$) δ(ppm): 5.83 (2H, bs), 7.05 (2H, d, J=9.0 Hz), 7.43 (1H, ddd, J=8.4, 4.4, 0.8 Hz), 7.46 (1H, ddd, J=8.4, 2.7, 1.6 Hz), 7.72 (2H, d, J=8.8 Hz), 8.39 (1H, dd, J=4.5, 1.5 Hz), 8.41 (1H, d, J=2.8 Hz), 9.64 (1H, bs). $^{13}$C NMR (125 MHz, DMSO-d$_6$) δ(ppm): 118.1 (CH), 124.8 (CH), 126.1 (CH), 127.4 (CH), 129.2, 134.5 (CH), 141.2 (CH), 144.9 (CH), 150.3, 153.0, 156.7. MS (FAB$^+$): 230 (MH$^+$). HRMS for $C_{12}H_{11}N_3O_2$ (MH$^+$): calculated: 230.0930; found 230.0941.

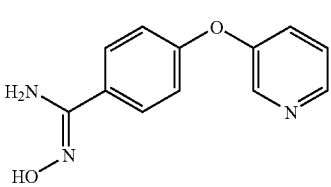 [SMILES: N/C(=N\O)c1ccc(Oc2cccnc2)cc1]

3-(4-(5-(4-(benzyloxy)phenyl)-1,2,4-oxadiazol-3-yl)phenoxy)pyridine (compound 47-structure shown below): (Z)-N'-Hydroxy-4-(pyridin-3-yloxy)benzamidine (206 mg, 89.9 μmol), N-dimethylaminopyridine (1.1 mg, 9.0 μmol) and 4-benzyloxybenzoyl chloride (28.8 mg, 116.8 μmol) were suspended in pyridine (5.0 mL) and the solution was refluxed for 45 hours. The reaction mixture was then cooled to room temperature, the solvent was removed under reduced pressure and the solid residue was purified by column chromatography (EtOAc/Hex 1:4) to give the product as a white solid (30 mg, 78%). $^1$H NMR (500 MHz, CDCL$_3$) δ(ppm): 5.16 (2H, s), 7.11 (2H, d, J=6.0 Hz), 7.12 (2H, d, J=6.2 Hz), 7.33-7.37 (2H, m), 7.39-7.46 (5H, m), 8.15 (2H, d, J=7.6 Hz), 8.17 (2H, d, J=7.4 Hz), 8.45 (1H, d, J=4.6 Hz), 8.49 (1H, d, J=2.4 Hz). $^{13}$C NMR (125 MHz, CDCL$_3$) δ(ppm): 70.4 (CH$_2$), 115.5 (CH), 117.2, 118.8 (CH), 123.0 (CH), 124.6, 126.8 (CH), 127.7 (CH), 128.5 (CH), 128.8, 128.9 (CH), 129.7 (CH), 130.3 (CH), 136.2, 141.9, 145.0, 159.1, 162.5, 168.3, 175.8. MS (FAB$^+$): 422 (MH$^+$). HRMS for $C_{26}H_{19}N_3O_3$ (MH$^+$): calculated: 422.1505; found 422.1521.

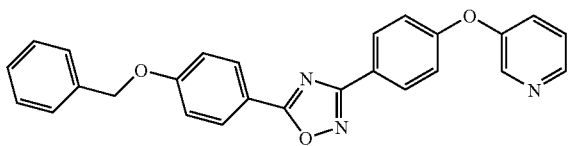 [SMILES: c1ccc(COc2ccc(-c3nc(-c4ccc(Oc5cccnc5)cc4)no3)cc2)cc1]

4-(3-(4-(pyridin-3-yloxy)phenyl)-1,2,4-oxadiazol-5-yl)phenol (compound 48-structure shown below): In a single neck round bottom flask fitted with a condenser, 3-(4-(5-(4-(Benzyloxy)phenyl)-1,2,4-oxadiazol-3-yl)phenoxy)pyridine (224 mg, 531 μmol) was suspended in methanol (5.0 mL) and THF (5.0 mL) and then 10% Pd/C (1.0 mg, 36 μmol) was added. The reaction vessel was sealed and the solution was stirred under H$_2$ at 55° C. for 23 hours. The hot solution was filtered through Celite and the pad was washed with methanol (20 mL). The solvent was removed under reduced pressure. The solid residue was purified by silica gel column chromatography (EtOAc/Hex 1:2) to give the product as a white solid (2 mg, 1%). $^1$H NMR (500 MHz, DMSO-d$_6$) δ(ppm): 7.00 (2H, d, J=9.0 Hz), 7.23 (1H, d, J=9.0 Hz), 7.05 (1H, ddd, J=8.4, 4.8, 0.8 Hz), 7.61 (1H, ddd, J=8.4, 2.8, 1.4 Hz), 8.02 (2H, d, J=9.0 Hz), 8.01 (2H, d, J=9.0 Hz), 8.46 (1H, dd, J=4.7, 1.3 Hz), 8.21 (1H, d, J=2.8 Hz) 10.58 (1H, s). MS (FAB$^+$): 332 (MH$^+$). HRMS for $C_{19}H_{13}N_3O_3$ (MH$^+$): calculated: 332.1035; found 332.1013.

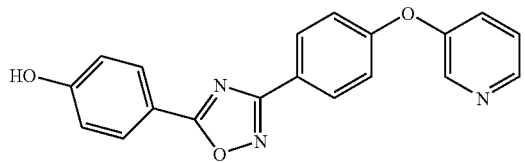 [SMILES: Oc1ccc(-c2nc(-c3ccc(Oc4cccnc4)cc3)no2)cc1]

4-(pyridin-4-yloxy)benzonitrile (compound 49-structure shown below): Potassium tert-butoxide (1.0 M in THF, 10.5 mL) was slowly added to a solution of 4-hydroxypyridine (997 mg, 10.5 mmol) in anhydrous DMSO (10.0 mL). After the mixture was stirred for 3 hours, a solution of 4-iodobenzonitrile (1.2 g, 5.2 mmol) in DMSO (10.0 mL) was added and the reaction mixture was heated at 160° C. for 44 hours. The mixture was cooled to room temperature and partitioned between methylene chloride (100 mL) and water (100 mL). The organic layer was separated and the aqueous layer was extracted with methylene chloride (2×100 mL). The organic layers were combined and concentrated in vacuo. The crude solid was purified by silica gel column chromatography (Hex/EtOAc 1:1) then (CH$_2$Cl$_2$/MeOH 98:2 to 96:4) to give the product as a light yellow solid (480 mg, 47%). $^1$H NMR (500 MHz, CDCL$_3$) δ(ppm): 6.52 (2H, d, J=8.0 Hz), 7.53 (2H, d, J=8.8 Hz), 7.64 (2H, d, J=8.0 Hz), 7.87 (2H, d, J=8.8 Hz). $^{13}$C NMR (125 MHz, CDCL$_3$) δ(ppm): 112.4, 117.6, 119.8 (CH), 123.2 (CH), 134.5 (CH), 138.2 (CH), 146.2, 179.0. MS (FAB$^+$): 197 (MH$^+$). HRMS for O$_{12}$H$_8$N$_2$O (MH$^+$): calculated: 197.0715; found 197.0716.

the product as a white solid (10 mg, 27%). $^1$H NMR (500 MHz, CDCL$_3$) δ(ppm): 5.18 (2H, s), 6.55 (2H, d, J=7.8 Hz), 7.14 (2H, d, J=9.0 Hz), 7.36-7.47 (5H, m), 7.50 (2H, d, J=8.6 Hz), 7.68 (2H, d, J=7.8 Hz), 8.17 (2H, d, J=8.8 Hz), 8.33 (2H, d, J=8.6 Hz). $^{13}$C NMR (125 MHz, CDCL$_3$) δ(ppm): 70.5 (CH$_2$), 115.7 (CH), 116.9, 119.5 (CH), 123.1 (CH), 127.6, 127.7 (CH), 128.6 (CH), 129.0 (CH), 129.7 (CH), 130.4 (CH), 136.1, 138.8 (CH), 145.1, 162.7, 167.7, 176.2, 179.3. MS (FAB$^+$): 422 (MH$^+$). HRMS for C$_{26}$H$_{19}$N$_3$O$_3$ (MH$^+$): calculated: 422.1505; found 422.1494.

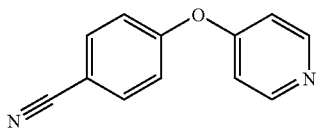 [SMILES: N#Cc1ccc(Oc2ccncc2)cc1]

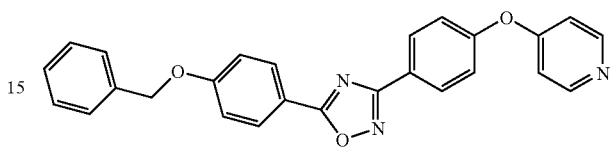

(Z)-N'-hydroxy-4-(pyridin-4-yloxy)benzamidine (compound 50-structure shown below): 4-(Pyridin-4-yloxy)benzonitrile (293 mg, 1.49 mmol) was dissolved in ethanol (6.0 mL) and hydroxylamine (197 mg, 5.97 mmol) was added. The mixture was refluxed for 3 hours and cooled to room temperature and then concentrated in vacuo to give the product which immediately formed white crystals and was taken to the next step without further purification. A small quantity was purified by column chromatography (Hex/EtOAc 1:8) to give the pure product (323 mg, 94%). $^1$H NMR (500 MHz, DMSO-d$_6$) δ(ppm): 5.95 (2H, s), 6.24 (2H, d, J=8.0 Hz), 7.56 (2H, d, J=8.8 Hz), 7.84 (2H, d, J=8.6 Hz), 8.02 (2H, d, J=7.8 Hz), 9.81 (1H, s). $^{13}$C NMR (125 MHz, DMSO-d$_6$) δ(ppm): 118.0 (CH), 122.1 (CH), 126.7 (CH), 132.6, 139.6 (CH), 142.8, 149.8, 177.4. MS (FAB$^+$): 230 (MH$^+$). HRMS for C$_{12}$H$_{11}$N$_3$O$_2$ (MH$^+$): calculated: 230.0930; found 230.0950.

4-(3-(4-(pyridin-4-yloxy)phenyl)-1,2,4-oxadiazol-5-yl)phenol (compound 52-structure shown below): In a single neck round bottom flask fitted with a condenser, 4-(4-(5-(4-(benzyloxy)phenyl)-1,2,4-oxadiazol-3-yl)phenoxy)pyridine (97 mg, 229 µmol) was suspended in methanol (3.0 mL) and THF (3.0 mL) 10% Pd/C (1 mg, 16 µmol) was added The reaction vessel was sealed and the solution was stirred under H$_2$ at 55° C. for 14 hours. The hot solution was filtered through Celite and the pad was washed with methanol (20 mL). The hot solution was filtered through Celite and the pad was washed with methanol (20 mL). The solvent was removed under reduced pressure the solid residue was purified by silica gel column chromatography (EtOAc/Hex 1:2) to give the product as a white solid (3 mg, 4%). $^1$H NMR (500 MHz, DMSO-d$_6$) δ(ppm): 6.57 (2H, d, J=7.8 Hz), 6.84 (1H, d, J=9.0 Hz), 7.50 (2H, d, J=8.8 Hz), 7.56 (2H, d, J=8.8 Hz), 7.75 (2H, d, J=8.8 Hz), 8.08 (2H, d, J=7.8 Hz).

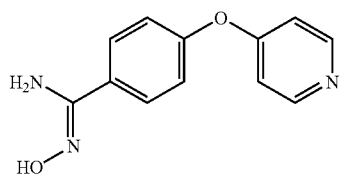 [SMILES: N/C(=N\O)c1ccc(Oc2ccncc2)cc1]

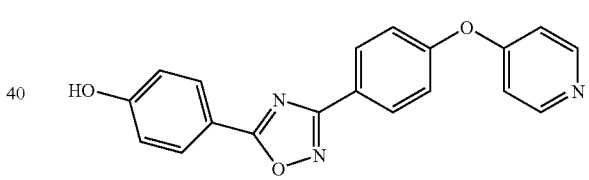

4-(4-(5-(4-(benzyloxy)phenyl)-1,2,4-oxadiazol-3-yl)phenoxy)pyridine (compound 51-structure shown below): (Z)-N'-Hydroxy-4-(pyridin-4-yloxy)benzamidine (20 mg, 88 µmol) and 4-benzyloxybenzoyl chloride (28 mg, 114 µmol) were suspended in pyridine (5.0 mL). The solution was refluxed for 21 hours, cooled to room temperature and the solvent was removed under reduced pressure. The solid residue was purified by silica gel column chromatography to give In accordance with embodiments of the present invention, a variety of compounds have been prepared and tested, as indicated, in part, by the description above. The tables below provide minimum inhibitory concentration data for the identified compounds tested against various bacterial strains.

Table 1 lists the active compounds and the activity of those compounds for a limited quantity of bacteria. Blank spaces indicate low or no activity.

TABLE 1

| Compound | S. aureus ATCC 29213 | E. faecalis 29212 | E. faecalis 29212 BH | E. faecalis 99 | E. faecal 99 BH | E. faecal 201 | E. faecal 201 BH |
|---|---|---|---|---|---|---|---|
| A |  | 125 |  |  |  | 128 |  |
| 1 | 2 (12B) | 2 | 16 | 2 | 8 | 2 | 16 |
| 2 | 2 | 4 |  | 4 |  | 4 |  |
| 7 |  | 32 |  |  | 512 | 128 |  |
| 14 |  | 128 (32) |  |  |  | 32 |  |
| 15 |  | 8 (128) |  |  |  | 128 |  |
| 19 |  | 64 |  |  |  | 128 |  |
| 25 |  | 256 |  |  |  | 256 |  |
| 26 |  | 64 |  |  |  | 128 |  |
| 27 |  |  |  |  |  | 256 |  |

TABLE 1-continued

| Compound | S. aureus ATCC 29213 | E. faecalis 29212 | E. faecalis 29212 BH | E. faecalis 99 | E. faecal 99 BH | E. faecal 201 | E. faecal 201 BH |
|---|---|---|---|---|---|---|---|
| 28 | 32 | | | | | 64 | |
| 29 | | 64 | | | | 128 | |
| 36 | | 64 (32) | | | | 32 | |
| 37 | | 500 (64) | 128 | | 500 | 32 | 500 |
| 40 | | | | | | 64 | |
| 43 | | | | | | 64 | |
| 44 | | | | | | 32 | |
| 47 | | | | | | 32 | |
| 48 | | | | | | 32 | |
| 51 | | | | | | 64 | |
| 52 | | | | | | 32 | |

Table 2 lists additional bacteria tested with compounds 1 and 2.

TABLE 2

| Compound | E. faecium 119-39A | E. faecium 119-39A BH | S. aureus NRS100 (COL) | S. aureus VAN1 | S. aureus VAN2 | E. faecium 106 | E. faecium 106 BH |
|---|---|---|---|---|---|---|---|
| 1 | 2 | 8 | 2 | 2 | 2 | 2 | 4 |
| 2 | 4 | | 2 | 2 | 2 | 4 | |

Figure 4:
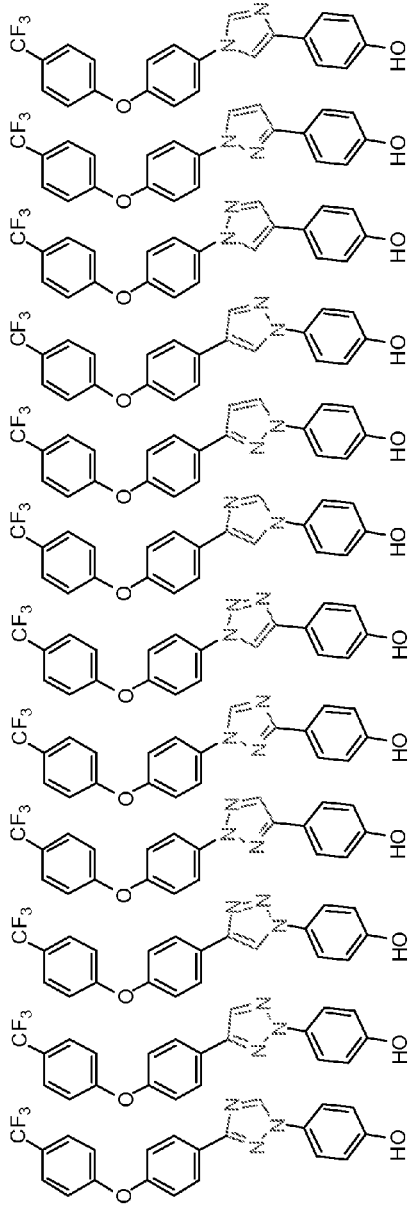
FIG. 4 illustrates antibacterial compounds in accordance with various embodiments of the present invention in which the five-member ring is modified.
Figure 4:
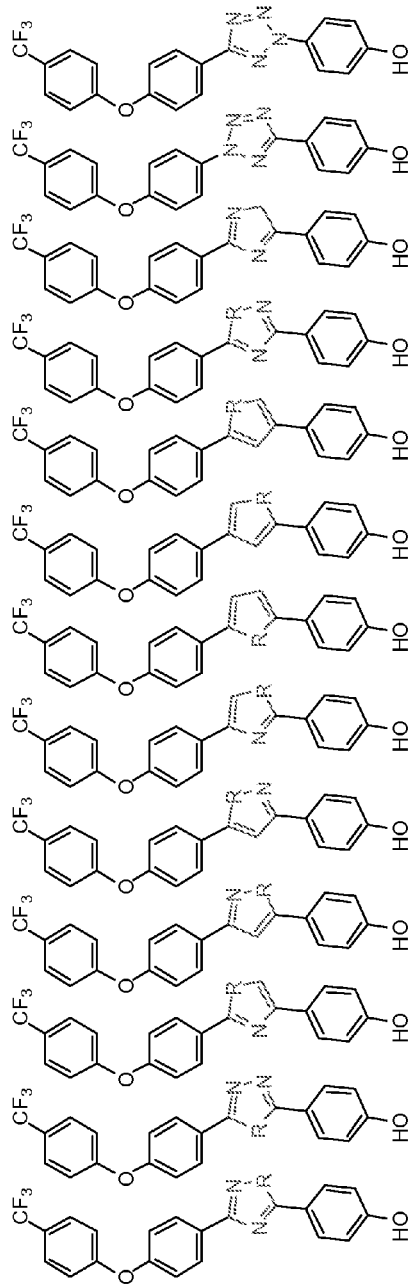

Additional analogues within the bounds of the claims of the present invention are provided in FIG. 4 where R=O, N, NH, S or CH$_2$. One of ordinary skill in the invention would be aware of further analogues of the compounds of FIG. 4 and the other compounds presented herein, and to the extent such analogues are encompassed by the claims as presented, such analogues are included herein.

Embodiments of the present invention also provide methods for inhibiting growth (reproduction, etc.) of bacteria using compounds described herein. As discussed above, compounds in accordance with embodiments of the present invention are designed to target penicillin-binding proteins. In other embodiments, compounds in accordance with embodiments of the present invention may be designed to target other biological process of bacteria.

In an embodiment, a method for inhibiting growth of bacteria is provided, comprising providing a source containing bacteria, and contacting the source with at least one compound, such as the compounds provided herein, as well as other compounds individually or in combination. In an embodiment, a source may be a human or an animal and a contacting operation may be performed in vivo in said human or animal, or may be performed in vitro on an extracted sample or testing sample. In an embodiment, gram positive bacteria, and, in particular the PBPs on gram positive bacteria, may be targeted for inhibition. In embodiments, strains of Entercoccus and/or Staphylococcus aureus may be targeted. In other embodiments, other bacterial strains may be targeted, such as but not limited to M. tuberculosis, B. anthraces, or others.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

What is claimed is:

1. A compound having the formula

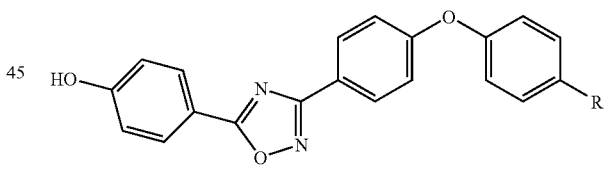

or a pharmaceutically acceptable salt thereof, wherein
R=H or CF$_3$.

2. The compound of claim 1 wherein R is H.

3. The compound of claim 1 wherein R is CF$_3$.

4. A pharmaceutical composition comprising a compound of claim 1 in combination with a pharmaceutically acceptable carrier.

5. A method for inhibiting growth of gram positive bacteria comprising contacting gram positive bacteria with a compound of claim 1, thereby inhibiting the growth of the bacteria.

6. The method of claim 5 wherein the contacting is performed in vivo in a human or animal.

7. The method of claim 6 wherein the gram positive bacteria is of the genus Enterococcus or Staphylococcus.

8. A compound of Formula (X):
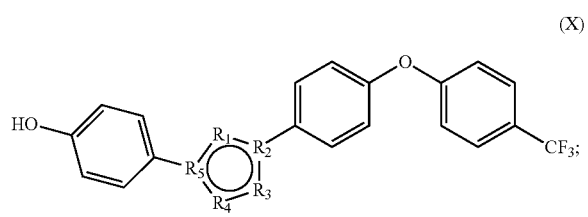
wherein
R$_2$ and R$_5$ are each independently C or N; and
R$_1$, R$_3$ and R$_4$ are each independently N or CH, provided that at least one of R$_1$-R$_5$ is C or CH;
or a pharmaceutically acceptable salt thereof.
9. The compound:
(A)
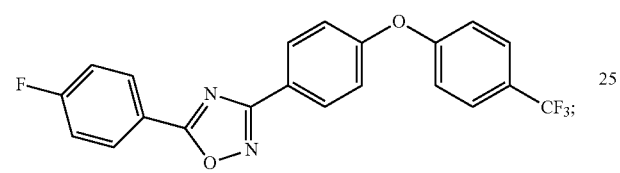
(1)
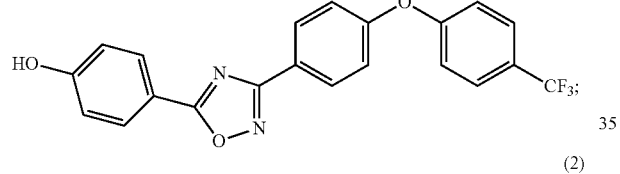
(2)
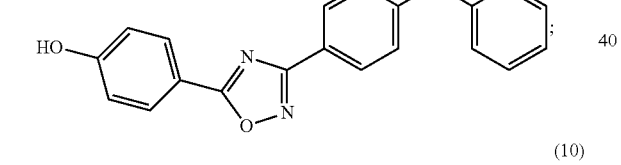
(10)
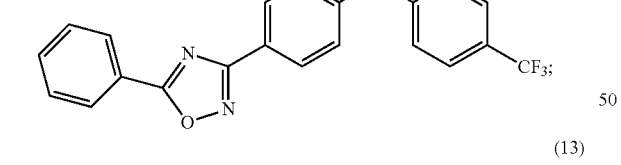
(13)
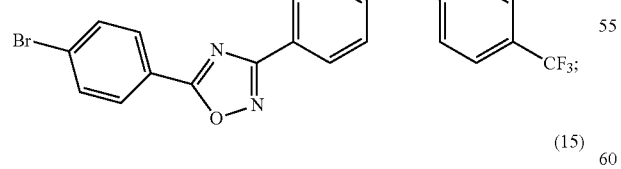
(15)
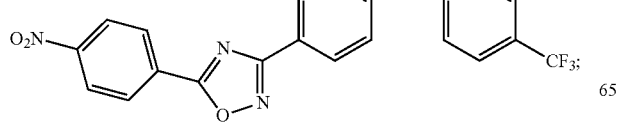
-continued
(16)
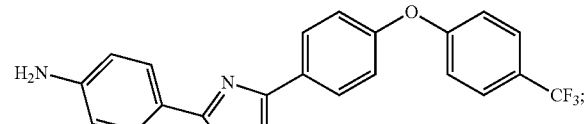
(19)
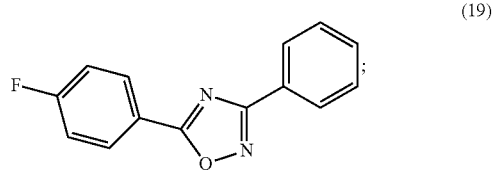
(22)
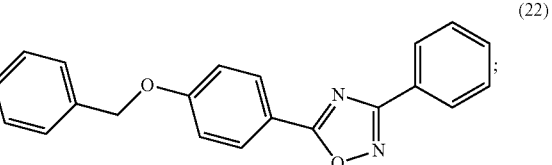
(26)
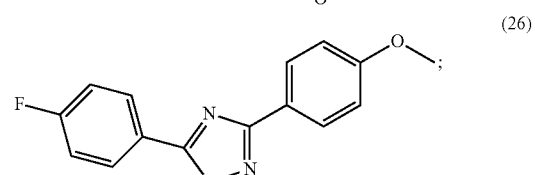
(27)
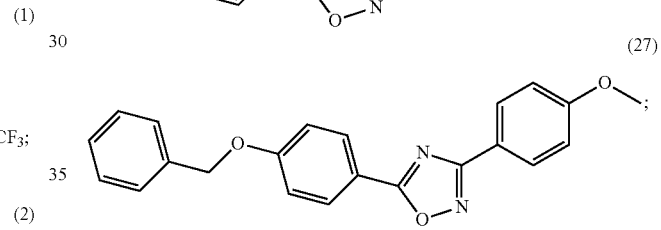
(28)
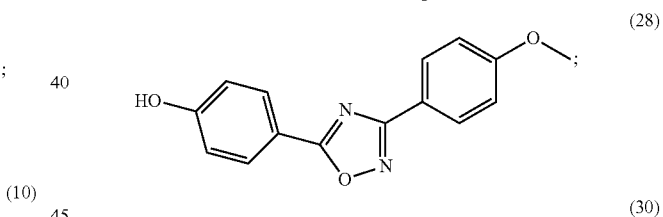
(30)
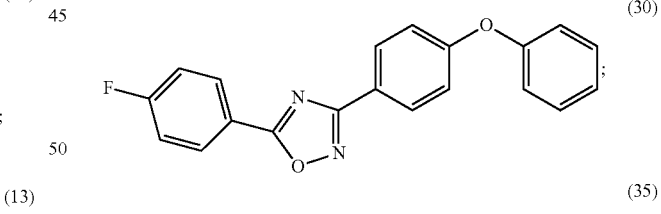
(35)
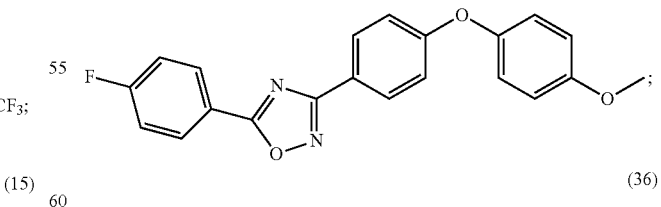
(36)
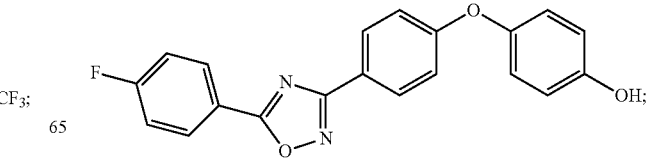

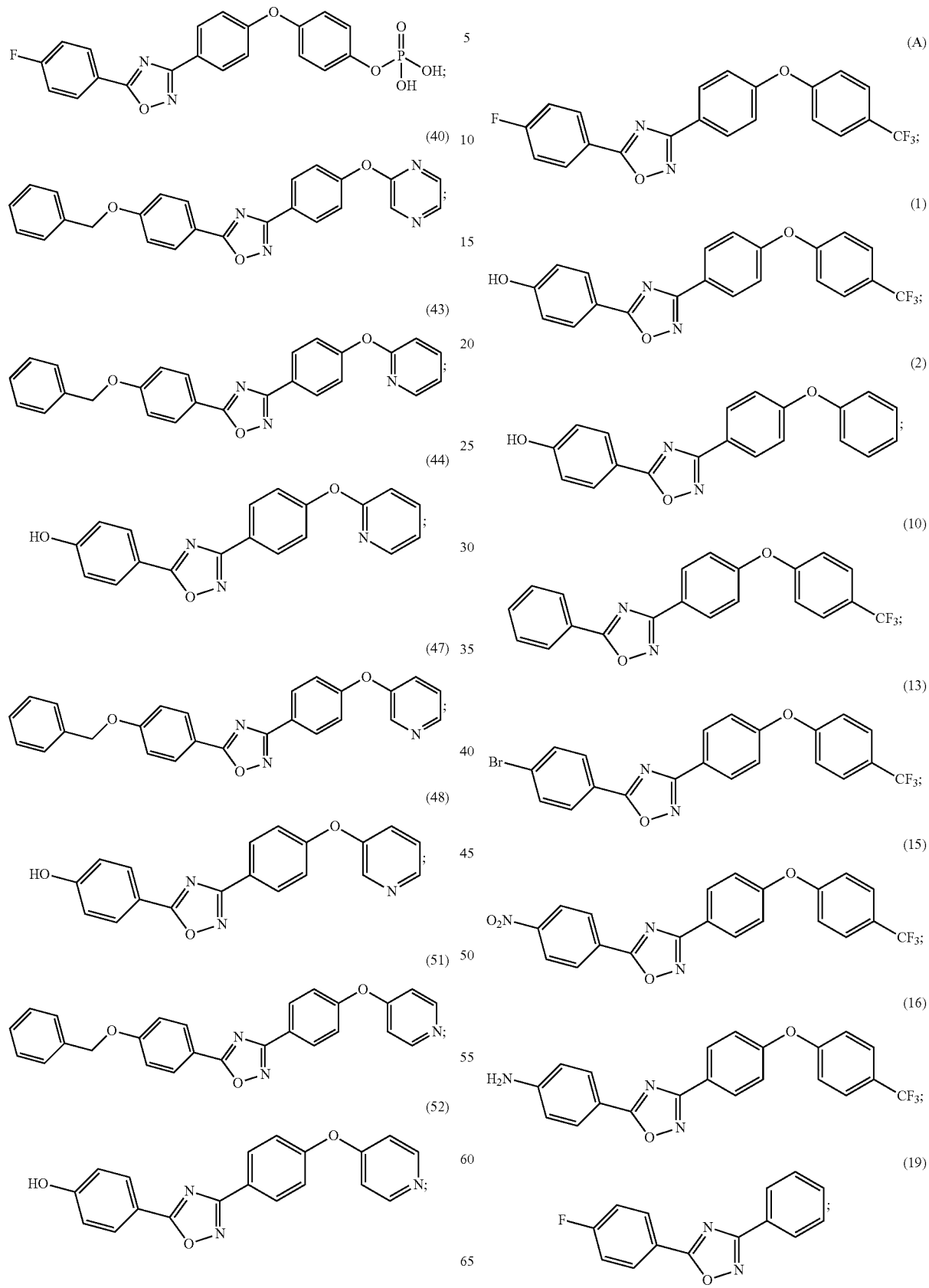
10. A pharmaceutical composition comprising the compound:
or a salt thereof.

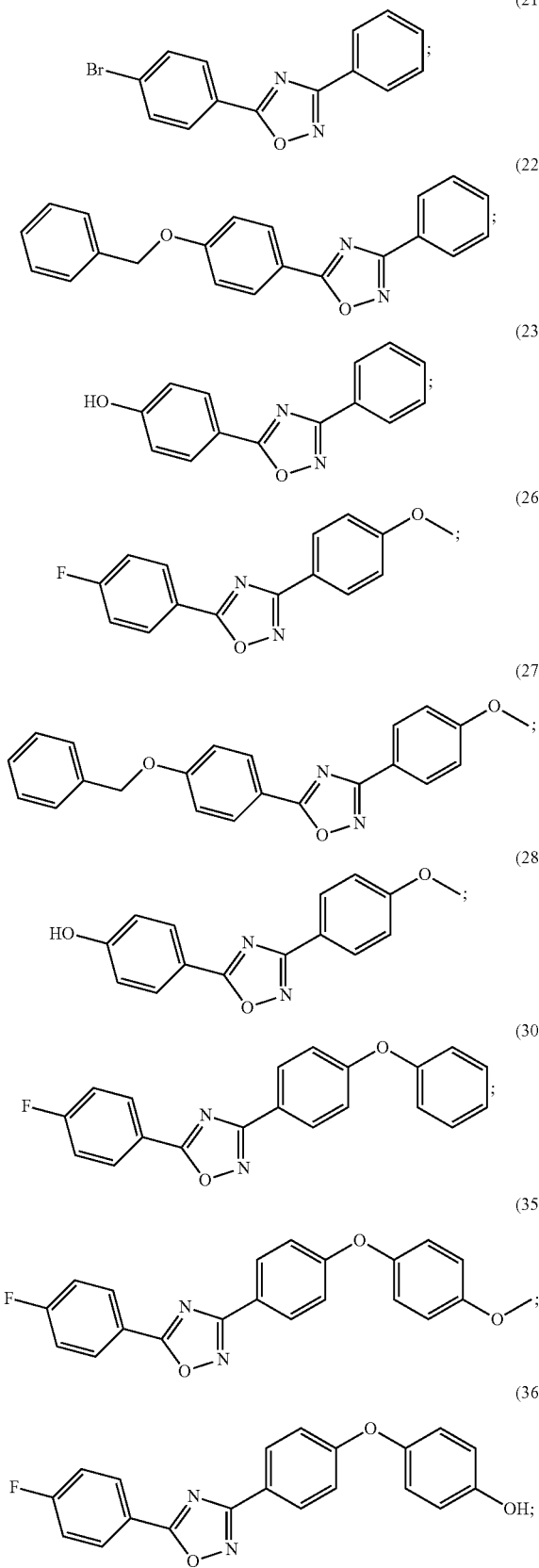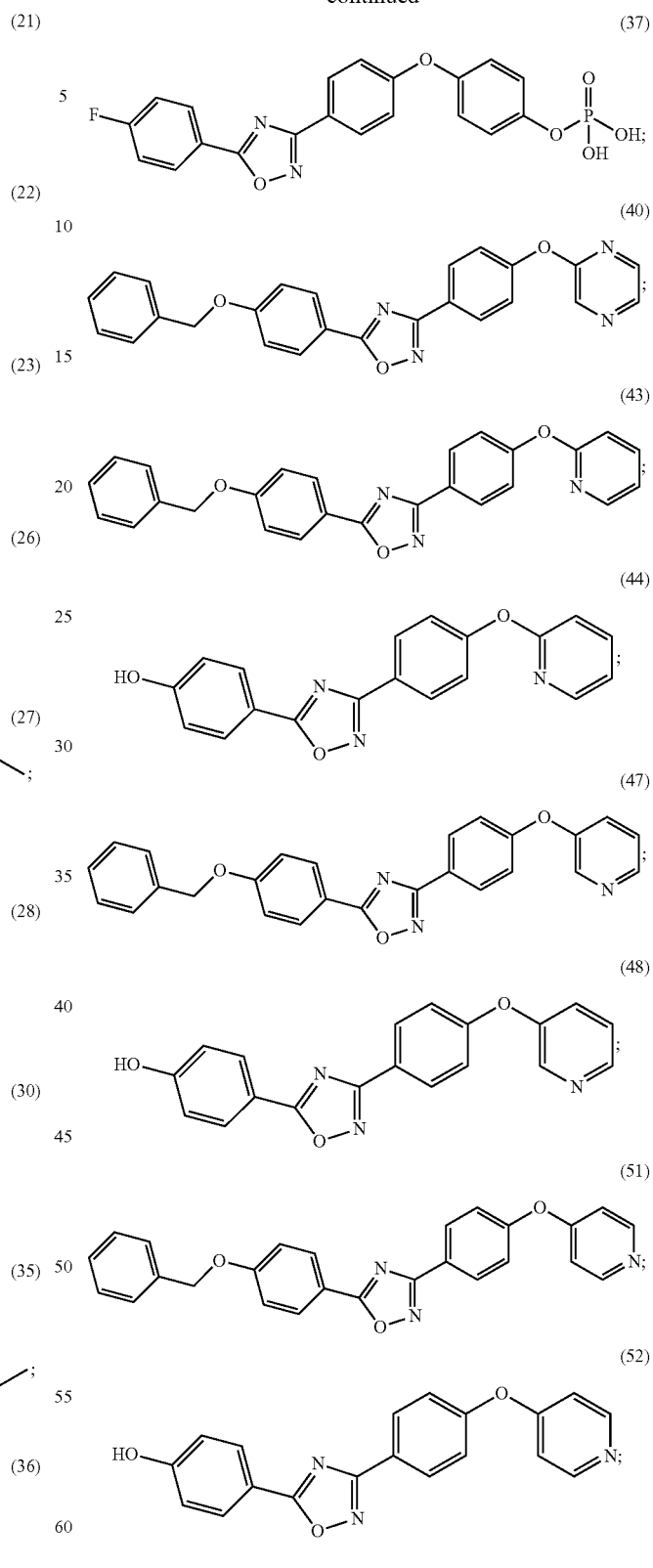
or a salt thereof; in combination with a pharmaceutically acceptable carrier.
* * * * *